(12) United States Patent
Haznadar et al.

(10) Patent No.: US 10,393,745 B2
(45) Date of Patent: Aug. 27, 2019

(54) METHOD FOR THE DIAGNOSIS AND PROGNOSIS OF CANCER

(71) Applicant: THE USA, AS REPRESENTED BY THE SECRETARY, DEPT. OF HEALTH AND HUMAN SERVICES, Bethesda, MD (US)

(72) Inventors: Majda Haznadar, Bethesda, MD (US); Ewy Mathe, Bethesda, MD (US); Andrew D. Patterson, Bethesda, MD (US); Curtis Craig Harris, Bethesda, MD (US); Frank Gonzalez, Bethesda, MD (US); Kristopher Krausz, Bethesda, MD (US); Soumen Manna, Bethesda, MD (US)

(73) Assignee: The USA, as represented by the Secretary, Department of Heath and Human Services, Bethesda, MD (US)

( * ) Notice: Subject to any disclaimer, the term of this patent is extended or adjusted under 35 U.S.C. 154(b) by 0 days.

(21) Appl. No.: 14/903,706

(22) PCT Filed: Jul. 11, 2014

(86) PCT No.: PCT/US2014/046294
§ 371 (c)(1),
(2) Date: Jan. 8, 2016

(87) PCT Pub. No.: WO2015/006657
PCT Pub. Date: Jan. 15, 2015

(65) Prior Publication Data
US 2016/0169899 A1    Jun. 16, 2016

Related U.S. Application Data

(60) Provisional application No. 61/845,055, filed on Jul. 11, 2013.

(51) Int. Cl.
*G01N 33/574*    (2006.01)

(52) U.S. Cl.
CPC ... *G01N 33/57423* (2013.01); *G01N 33/5743* (2013.01); *G01N 33/57488* (2013.01); *G01N 2400/00* (2013.01); *G01N 2800/52* (2013.01)

(58) Field of Classification Search
CPC .......... G01N 2800/50; G01N 2800/52; G01N 2800/56; G01N 2800/60; G01N 33/574; G01N 33/57423; G01N 33/5743; G01N 33/57488; G01N 2400/00
See application file for complete search history.

(56) References Cited

U.S. PATENT DOCUMENTS

2011/0240842 A1    10/2011    Grant et al.

FOREIGN PATENT DOCUMENTS

| CN | 103033580 | 4/2013 |
|---|---|---|
| WO | WO 2011/128256 | 10/2011 |
| WO | WO 2014/116833 | 7/2014 |

OTHER PUBLICATIONS

Zhang, Jian et al. "Esophageal cancer metabolite biomarkers detected by LC-MS and NMR methods." PLoS ONE (2012) 7 e30181.*
Xiao, Jun Feng et al. "Metabolite Identification and Quantitation in LC-MS/MS-based metabolomics." Trends Analyt Chem. (2012) 32 1-14. (Year: 2012).*
Database Registry [Online] Chemical Abstracts Service, Columbus, Ohio, US; Jul. 23, 2014 (Jul. 23, 2014), "beta-D-Ribofuranosylcreatine", XP002731178, Database accession No. 1616693-92-5 abstract.
"Lung Cancer Staging," American Joint Committee on Cancer, © 2009, 2 pages.
An et al. "Integrated ionization approach for RRLC-MS/MS-based metabonomics: finding potential biomarkers for lung cancer." Journal of Proteome Research, Aug. 2010, vol. 9, No. 8, pp. 4071-4081 (Abstract Only).
Arscott et al. Analysis of urinary exosomes to identify new markers of non-small-cell lung cancer. Biomarkers in Medicine, Dec. 2011, vol. 5, No. 6, p. 822 (Abstract Only).
Balasubramaniyan et al. "Diagnostic and prognostic role of plasma and urinary sialic acid in human carcinoma of uterine cervix." Biochemistry and Molecular Biology International Journal, Jul. 1994, vol. 33, No. 4, pp. 617-623 (Abstract Only).
Bradshaw et al. "Steroid secretory characteristics of a virilizing adrenal adenoma in a woman." Journal of Endocrinology, Feb. 1994, vol. 140, No. 2, pp. 297-307 (Abstract Only).
Ding et al. "Lectin-histochemical reactivity of sialic acid in breast cancer and its relationship to prognosis using limulus polyphemus agglutinin," International Journal of Oncology, Apr. 1997, vol. 10, No. 4, pp. 759-763 (Abstract Only).
Dolara et al. "Variations of cortisol hydroxylation and paracetamol metabolism in patients with bladder carcinoma." British Journal of Urology, Nov. 1988, vol. 62, No. 5, pp. 419-426 (Abstract Only).
Feijoo-Carnero et al. "Clinical significance of preoperative serum sialic acid levels in colorectal cancer: utility in the detection of patients at high risk of tumor recurrence." The International Journal of Biological Markers, Jan.-Mar. 2004, vol. 19, No. 1, pp. 38-45 (Abstract Only).

(Continued)

*Primary Examiner* — Christopher Adam Hixson
(74) *Attorney, Agent, or Firm* — Sheridan Ross P.C.

(57) ABSTRACT

The present invention provides methods and materials for diagnosing cancer in an individual using a tissue, blood or urine sample from the patient. Specifically, the disclosed method comprises determining the level of one or more metabolite selected from the group consisting of creatine riboside, metabolite 561+, Cortisol sulfate and N-acetylneuraminic acid. The present invention also provides a method for determining the prognosis of a cancer patient by determining the level of one or more metabolite selected from the group consisting of creatine riboside, metabolite 561+, Cortisol sulfate and N-acetylneuraminic acid. Also provided are kits for detecting cancer or determining the prognosis of a cancer patient.

20 Claims, 31 Drawing Sheets

(56) References Cited

OTHER PUBLICATIONS

Feldman et al. "Urinary free cortisol exretion in patients with metastatic cancer." The American Journal of the Medical Sciences, Sep.-Oct. 1979, vol. 278, No. 2, pp. 149-152 (Abstract Only).
Francini et al. "Circulating levels of immunoreactive peptides and steroid hormones in bronchogenic carcinoma." The International Journal of Biological Markers, May-Aug. 1986, vol. 1, No. 2, pp. 93-100 (Abstract Only).
Ghosh et al. "Abnormal Exretion of Cortiscosteroid Sulphates in Patients with Breast Cancer," British Medical Journal, Feb. 1973, pp. 328-330.
Hanai et al. "Urinary volatile compounds as biomarkers for lung cancer." Bioscience, Biotechnology, and Biochemistry, 2012, vol. 76, No. 4, pp. 679-684 (Abstract Only).
Harvey et al. "Glycoproteins and human cancer: II. Correlation between circulating level and disease status." Cancer, Jan. 1981, vol. 47, No. 2, pp. 324-327 (Abstract Only).
Jones et al. "Determination of dehydroepiandrosterone and dehydroepiandrosterone sulphate in blood and tissue. Studies of normal women and women with breast or endometrial cancer." Journal of Steroid Biochemistry, Jan. 1987, vol. 26, No. 1, pp. 151-159 (Abstract Only).
Koc et al. "Salivary sialic acid and cancer." J Marmara Univ Dent Fac, Sep. 1996, vol. 2, No. 2-3, pp. 523-526 (Abstract Only).
Konukoglu et al. "Urinary excretion of sialic acid in patients with bladder tumors." Cancer Letters, Jul. 1995, vol. 94, No. 1, pp. 97-100 (Abstract Only).
Krolikowski et al. "Serum sialic acid levels in lung cancer patients." Pharmacology, 1976, vol. 14, No. 1, pp. 47-51 (Abstract Only).
Mathe, E.A., et al., "Noninvasive Urinary Metabolomic Profiling Identifies Diagnostic and Prognostic Markers in Lung Cancer", Cancer Research, vol. 7 4, No. 12, Apr. 15, 2014 (Apr. 15, 2014), pp. 3259-3270, XP055146640.
Matsumura et al. "Urinary Volatile Compounds as Biomarkers for Lung Cancer: A Proof of Principle Study Using Odor Signatures in Mouse Models of Lung Cancer," PLOS One, Jan. 2009, vol. 5, No. 1, 11 pages.
Narayanan "Sialic Acid as a Tumor Marker." Annals of Clinical & Laboratory Science, Jul./Aug. 1994, vol. 24, No. 4, pp. 376-384 (Abstract Only).
Patel et al. "Comparison between serum levels of carcinoembryonic antigen, sialic acid and phosphohexose isomerase in lung cancer." Neoplasma, 1995, vol. 42, No. 5, pp. 271-274 (Abstract Only).
Raval et al. "Evaluation of serum sialic acid, sialyltransferase and sialoproteins in oral cavity cancer." Oral Diseases, May 2003, vol. 9, No. 3, pp. 119-28 (Abstract Only).
Read et al. "Salivary cortisol and dehydroepiandrosterone sulphate levels in postmenopausal women with primary breast cancer." European Journal of Cancer and Clinical Oncology, Apr. 1983, vol. 19, No. 4, pp. 477-483 (Abstract Only).
Rocha et al. "Exploring the human urine metabolomic potentialities by comprehensive two-dimensional gas chromatography coupled to time of flight mass spectrometry." Journal of Chromatography A, Aug. 2012, vol. 1252, pp. 155-163 (Abstract Only).
Rose et al. "The Urinary Excretion of Corticosteroid Sulfates by Cancer Patients," Cancer, Dec. 1975, vol. 36, No. 6, pp. 2060-2063.
Schatzl et al. "Endocrine Patterns in Patients with Benign and Malignant Prostatic Diseases," The Prostate, Aug. 2000, vol. 44, No. 3, pp. 219-224.
Shimada et al. "Elevation of ratio of urinary N-acetylneuraminlactose to free sialic acid in some advanced cancer patients." Journal of Gastroenterology, Feb. 1995, vol. 30, No. 1, pp. 21-27 (Abstract Only).
Stancakova et al. "Urinary Free Cortisol, Cortisone, Cortisol Sulfate, Coritsone Sulfate and 17-Ketosteroids in Breast Cancer," Neoplasma, 1979, vol. 26, No. 2, pp. 205-213.
Tantipaiboonwong et al. "Differnet techniques for urinary protein analysis of normal and lung cancer patients." Proteomics, Mar. 2005, vol. 5, No. 4, pp. 1140-1149 (Abstract Only).
Yang et al. "Urinary metabonomic study of lung cancer by a fully automatic hyphenated hydrophilic interaction/RPLC-MS system." Journal of Separation Science, Jun. 2010, vol. 33, No. 10, pp. 1495-1503 (Abstract Only).
International Search Report and Written Opinion for International (PCT) Patent Application No. PCT/US14/46294, dated Jan. 20, 2015 15 pages.
International Preliminary Report onf Patentability for International (PCT) Patent Application No. PCT/US2014/046294, dated Jan. 21, 2016 10 pages.

* cited by examiner

A.

| | | |
|---|---|---|
| | | Primary Tumor |
| | TX | Primary tumor cannot be assessed, or tumor proven by the presence of malignant cells in sputum or bronchial washings but not visualized by imaging or bronchoscopy |
| | T0 | No evidence of primary tumor |
| | Tis | Carcinoma in situ |
| | T1 | Tumor 3 cm or less in greatest dimension surrounded by lung or visceral pleura, without bronchoscopic evidence of invasion more proximal than the lobar bronchus (for example not in the main bronchus) |
| | T1a | Tumor 2 cm or less in greatest dimension |
| | T1b | Tumor more than 2 cm but 3 cm or less in greatest dimension |
| | T2 | Tumor more than 3 cm but 7cm or less or tumor with any of the following features (T2 tumors with these features are classified T2a if 5 cm or less); involves main bronchus, 2 cm or more distal to the carina; invades visceral pleura (PL1 r PL2); associate with atelectasis or obstructive pneumonitis that extends to the hilar region but does not involve the entire lung |
| | T2a | Tumor more than 3 cm but 5 cm or less in greatest dimension |
| | T2b | Tumor more than 5 cm but 7 cm or less in greatest dimension |
| | T3 | Tumor more than 7 cm or one that directly invades any of the following: parietal pleura (PL3), chest wall (including superior sulcus tumors), diaphragm, phrenic nerve, mediastinal pleura, parietal pericardium,; or tumor in the main bronchus less than 2 cm distal to the carina but without involvement of the carina; or associated atelectasis or obstructive pneumonitis of the entire lung or separate tumor nodule(s) in the same lobe |
| | T4 | Tumor of any size that invades any of the following: mediastinum, heart, great vessels, trachea, recurrent laryngeal nerve, esophagus, vertebral body, carina, separate tumor nodule(s) in a different ipsilateral lobe |
| | | Distant Metastasis |
| | M0 | No distant metastasis |
| | M1 | Distant metastasis |
| | M1a | Separate tumor nodule(s) in a contralateral lobe, tumor with pleural nodules or malignant pleural (or pericardial) effusion |
| | M1b | Distant metastasis (in extrathoracic organs) |
| | | Regional Lymph Nodes |
| | NX | Regional lymph node cannot be assessed |
| | N0 | No regional lymph node metastasis |
| | N1 | Metastasis in ipsilateral peribronchial and/or ipsilateral hilar lymph nodes and intrapulmonary nodes, including involvement by direct extension |
| | N2 | Metastasis in ipsilateral mediastinal and/or subcarinal lymph nodes |
| | N3 | Metastasis in contralateral mediastinal, contralateral hilar, ipsilateral of contralateral scalene, or supraclavicular lymph node(s) |

| | | | |
|---|---|---|---|
| Occult carcinoma | TX | N0 | M0 |
| Stage 0 | Tis | N0 | M0 |
| Stage IA | T1a | N0 | M0 |
| | T1b | N0 | M0 |
| Stage IB | T2a | N0 | M0 |
| Stage IIA | T2b | N0 | M0 |
| | T1a | N1 | M0 |
| | T1b | N1 | M0 |
| | T2a | N1 | M0 |
| Stage IIB | T2b | N1 | M0 |
| | T3 | N0 | M0 |
| Stage IIIA | T1a | N2 | M0 |
| | T1b | N2 | M0 |
| | T2a | N2 | M0 |
| | T2b | N2 | M0 |
| | T3 | N1 | M0 |
| | T3 | N2 | M0 |
| | T4 | N0 | M0 |
| | T4 | N1 | M0 |
| Stage IIIB | T1a | N3 | M0 |
| | T1b | N3 | M0 |
| | T2a | N3 | M0 |
| | T2b | N3 | M0 |
| | T3 | N3 | M0 |
| | T4 | N3 | M0 |
| | T4 | N3 | M0 |
| Stage IV | Any T | Any N | M1a |
| | Any T | Any N | M1b |

Creatine
Riboside

A.
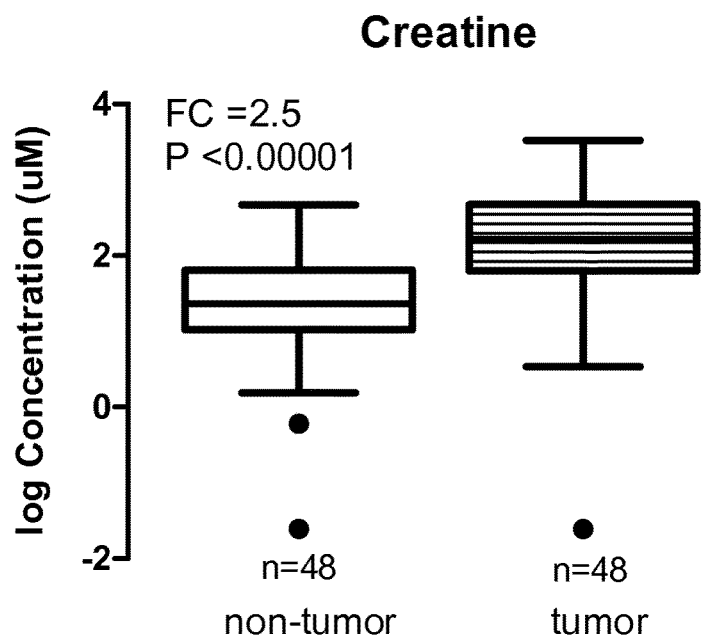
B. Correlation of Creatine Riboside and Creatine in the Tissue Set
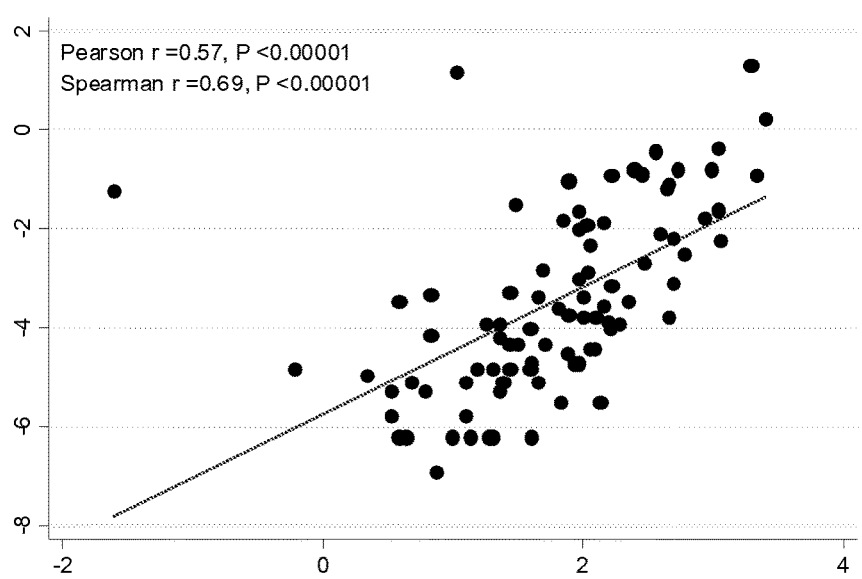
Fig. 7

A.

*All Cases (N =469)*

| Metabolite | Controls N (%) | Cases N (%) | Univariate | | | Multivariate* | | |
|---|---|---|---|---|---|---|---|---|
| | | | OR (95% CI) | P | FDR† | OR (95% CI) | P | FDR† |
| Creatine riboside | 134 (25.0) | 304 (64.82) | 5.50 (4.21, 7.26) | 8.35E-35 | 2.64E-31 | 5.05 (3.57, 7.14) | 4.93E-20 | 1.56E-16 |
| Cortisol sulfate | 134 (25.0) | 227 (48.40) | 2.84 (2.17, 3.71) | 1.69E-14 | 2.68E-11 | 2.56 (1.83, 3.58) | 3.52E-08 | 2.79E-05 |
| N-acetylneuraminic acid | 134 (25.0) | 213 (34.8) | 2.50 (1.91, 3.26) | 1.87E-11 | 5.38E-09 | 2.13 (1.52, 2.98) | 1.11E-05 | 1.25E-03 |
| 561+ | 134 (25.0) | 201 (34.1) | 2.25 (1.72, 2.94) | 2.90E-09 | 4.37E-07 | 1.89 (1.34, 2.67) | 3.17E-04 | 0.01 |

*Stage I-II Cases (N =213)*

| Metabolite | Controls N (%) | Cases N (%) | Univariate | | | Multivariate* | | |
|---|---|---|---|---|---|---|---|---|
| | | | OR (95% CI) | P | FDR† | OR (95% CI) | P | FDR† |
| Creatine riboside | 134 (23.6) | 116 (54.5) | 3.59 (2.57, 5.01) | 5.59E-14 | 1.77E-10 | 3.34 (2.07, 5.39) | 7.85E-07 | 0.002 |
| Cortisol sulfate | 134 (23.6) | 88 (41.3) | 2.11 (1.51, 2.95) | 1.26E-05 | 0.003 | 1.84 (1.14, 2.98) | 0.013 | 0.295 |
| N-acetylneuraminic acid | 134 (23.6) | 74 (34.7) | 1.60 (1.13, 2.25) | 0.007 | 0.076 | 1.72 (1.05, 2.81) | 0.030 | 0.347 |
| 561+ | 134 (23.6) | 76 (35.7) | 1.66 (1.18, 2.34) | 0.003 | 0.046 | 1.30 (0.80, 2.12) | 0.296 | 0.728 |

\* Adjusted for race, gender, interview year, smoking status, pack years, and urine collection time
† False discovery rate (FDR) based on Benjamini and Hochberg

*Stage I Cases (N= 144)*

| Signal | Univariate | | Multivariate* | |
|---|---|---|---|---|
| | HR (95% CI) | P | HR (95% CI) | P |
| N-acetylneuraminic acid | 0.62 (0.30 - 1.27) | 0.19 | 0.44 (0.19 - 0.99) | 0.05 |
| Cortisol sulfate | 1.51 (0.80 - 2.85) | 0.21 | 1.46 (0.72 - 2.96) | 0.30 |
| Creatine riboside | 1.40 (0.74 - 2.62) | 0.08 | 1.49 (0.72 - 3.11) | 0.29 |
| 561+ | 1.06 (0.53 - 2.10) | 0.87 | 1.93 (0.84 - 4.46) | 0.12 |

*Stage II Cases (N =69)*

| Signal | Univariate | | Multivariate* | |
|---|---|---|---|---|
| | HR (95% CI) | P | HR (95% CI) | P |
| N-acetylneuraminic acid | 0.89 (0.41 - 1.94) | 0.77 | 1.33 (0.54 - 3.28) | 0.54 |
| Cortisol sulfate | 1.17 (0.58 - 2.37) | 0.66 | 1.24 (0.53 - 2.92) | 0.63 |
| Creatine riboside | 2.36 (1.05 - 5.31) | 0.04 | 2.89 (1.01 - 8.23) | 0.05 |
| 561+ | | | | |
| <= 15 months | 11.96 (1.49 - 95.94) | 0.02 | 11.25 (1.28 - 99.26) | 0.03 |
| > 15 months | 1.00 (0.41 - 2.46) | 0.99 | 1.03 (0.33 - 3.23) | 0.97 |

*Stage III-IV Cases (N =103)*

| Signal | Univariate | | Multivariate* | |
|---|---|---|---|---|
| | HR (95% CI) | P | HR (95% CI) | P |
| N-acetylneuraminic acid | 1.59 (1.05 - 2.41) | 0.03 | 2.41 (1.36 - 4.26) | 0.002 |
| Cortisol sulfate | 1.45 (0.96 - 2.20) | 0.08 | 1.85 (1.09 - 3.13) | 0.02 |
| Creatine riboside | | | | |
| <= 15 months | 2.62 (1.16 - 5.89) | 0.02 | 2.78 (1.15 - 6.72) | 0.02 |
| > 15 months | 0.66 (0.37 - 1.17) | 0.16 | 0.69 (0.33 - 1.42) | 0.31 |
| 561+ | 1.12 (0.74 - 1.69) | 0.60 | 1.31 (0.76 - 2.25) | 0.33 |

* Adjusted for gender, race, histology, smoking status, pack years, interview year and urine collection time

*All Cases (N= 92)*

| Signal | Univariate | | Multivariate* | |
|---|---|---|---|---|
| | HR (95% CI) | P | HR (95% CI) | P |
| N-acetylneuraminic acid | 1.73 (1.00 - 3.03) | 0.05 | 1.68 (0.88 - 3.20) | 0.11 |
| Cortisol sulfate | 1.65 (0.97 - 2.82) | 0.067 | 1.42 (0.77 - 2.60) | 0.26 |
| Creatine riboside | 2.03 (1.11 - 3.69) | 0.02 | 2.21 (1.12 - 4.37) | 0.02 |
| 561+ | 1.30 (0.74 - 2.13) | 0.39 | 1.49 (0.77 - 2.88) | 0.24 |

* Adjusted for gender, race, stage, histology, smoking status, pack years, interview year and urine collection time

Fig. 13-3

Liver
*N cases = 98; N controls = 100*

| Metabolite‡ | Controls N (%) | Cases N (%) | Univariate OR (95% CI) | P | Multivariate* OR (95% CI) | P |
|---|---|---|---|---|---|---|
| Creatine riboside | 25 (25.0) | 82 (83.7) | 15.4 (7.6, 31.0) | <0.0001 | 9.8 (3.4, 28.6) | <0.0001 |
| Cortisol sulfate | 25 (25.0) | 85 (86.7) | 19.6 (9.4, 41.1) | <0.0001 | 46.9 (12.1, 182.3) | <0.0001 |
| N-acetylneuraminic acid | 25 (25.0) | 71 (72.5) | 7.9 (4.2, 14.9) | <0.0001 | 10.2 (3.4, 31.1) | <0.0001 |
| 561+ | 25 (25.0) | 90 (91.8) | 33.8 (14.4, 79.2) | <0.0001 | 65.6 (15.4, 280.2) | <0.0001 |

Prostate
*N cases = 99; N controls = 98*

| Metabolite‡ | Controls N (%) | Cases N (%) | Univariate OR (95% CI) | P | Multivariate* OR (95% CI) | P |
|---|---|---|---|---|---|---|
| Creatine riboside | 24 (24.5) | 51 (51.5) | 3.3 (1.8, 6.0) | <0.0001 | 2.2 (0.9, 5.1) | 0.08 |
| Cortisol sulfate | 24 (24.5) | 39 (39.4) | 2.0 (1.1, 3.7) | 0.03 | 2.8 (1.2, 6.5) | 0.01 |
| N-acetylneuraminic acid | 25 (25.5) | 36 (36.4) | 1.7 (0.9, 3.1) | 0.10 | 1.1 (0.5, 2.5) | 0.83 |
| 561+ | 25 (25.5) | 39 (39.4) | 1.9 (1.0, 3.5) | 0.04 | 1.4 (0.6, 3.2) | 0.59 |

* Adjusted for race, gender (in liver analysis only), interview year, smoking status and pack years
‡ Levels dichotomized into high and low based on the 75th percentile of population control abundances (low = referent)

Fig. 17

METHOD FOR THE DIAGNOSIS AND PROGNOSIS OF CANCER

CROSS REFERENCE TO RELATED APPLICATIONS

This application is a national stage application under 35 U.S.C. 371 and claims the benefit of PCT Application No. PCT/US2014/046294 having an international filing date of Jul. 11, 2014, which designated the United States, which PCT application claimed the benefit of U.S. Provisional Application No. 61/845,055 filed Jul. 11, 2013, the disclosure of each of which are incorporated herein by reference.

FIELD OF INVENTION

The present invention relates to the use of specific biomarkers in the detection of cancer and the prediction of the prognosis of cancer patients.

SUMMARY OF INVENTION

Methods of the present invention relate to the use of specific biomarkers to detect the presence of cancer in an individual. The disclosed methods are also useful for determining the prognosis of an individual known to have cancer. In particular, methods of the present invention may generally be accomplished by determining the levels of one or more specific biomarkers, disclosed herein, within an individual. Alterations in these levels relative to the levels of the same one or more biomarkers in individuals known to be free of cancer are indicative of the presence of cancer.

One embodiment of the present invention is a method for the detection of cancer, comprising determining the level of at least two compounds selected from the group consisting of creatine riboside, metabolite 561+, cortisol sulfate and N-acetylneuraminic acid, in a sample obtained from an individual, wherein elevated levels of the at least two compounds indicates the presence of cancer. In one embodiment, the method comprises determining the level of at least three compounds selected from the group consisting of creatine riboside, metabolite 561+, cortisol sulfate and N-acetylneuraminic acid in a sample obtained from an individual, wherein elevated levels of the at least three compounds indicates the presence of cancer. In one embodiment the method comprises determining the level of creatine riboside, metabolite 561+, cortisol sulfate and N-acetylneuraminic acid in a sample obtained from an individual, wherein elevated levels of all four compounds indicates the presence of cancer. In one embodiment, the cancer is lung cancer. In one embodiment, the cancer comprises adenocarcinoma. In one embodiment, the cancer comprises squamous cell carcinoma. In one embodiment, the sample is body tissue. In one embodiment, the sample is a body fluid. In one embodiment, the sample is urine. In one embodiment, the sample is selected from the group consisting of blood, serum and plasma.

One embodiment of the present invention is a method for the detection of cancer comprising determining the level of one or more compounds selected from the group consisting of creatine riboside and metabolite 561+, in a sample from an individual, wherein elevated levels of creatine riboside and/or metabolite 561+ indicate the presence of cancer. In one embodiment, the method comprises determining the levels of creatine riboside and metabolite 561+, in a sample, wherein elevated levels of creatine riboside and metabolite 561+ indicate the presence of cancer. In one embodiment, the cancer is lung cancer. In one embodiment, the cancer comprises adenocarcinoma. In one embodiment, the cancer comprises squamous cell carcinoma. In one embodiment, the sample is body tissue. In one embodiment, the sample is a body fluid. In one embodiment, the sample is urine. In one embodiment, the sample is selected from the group consisting of blood, serum and plasma.

One embodiment of the present invention is a method for the detection of lung cancer comprising determining the level of cortisol sulfate in a sample obtained from an individual, wherein an elevated level of cortisol sulfate indicates the presence of lung cancer. In one embodiment, the cancer comprises adenocarcinoma. In one embodiment, the cancer comprises squamous cell carcinoma. In one embodiment, the sample is body tissue. In one embodiment, the sample is a body fluid. In one embodiment, the sample is urine. In one embodiment, the sample is selected from the group consisting of blood, serum and plasma.

One embodiment of the present invention is a method for the detection of lung cancer, comprising determining the level of N-acetylneuraminic acid in urine from an individual, wherein an elevated level of urinary N-acetylneuraminic acid indicates the presence of lung cancer. In one embodiment, the N-acetylneuraminic acid is N-acetylneuraminic acid. In one embodiment, the cancer comprises adenocarcinoma. In one embodiment, the cancer comprises squamous cell carcinoma.

One embodiment of the present invention is a method for monitoring the efficacy of a cancer treatment, the method comprising:
 a) determining the level of one or more biomarkers selected from the group consisting of creatine riboside, metabolite 561+, cortisol sulfate and N-acetylneuraminic acid in a sample patient having cancer to obtain a pre-treatment level of the one or more biomarkers;
 b) administering a cancer treatment to the patient;
 c) determining the level of the one or more biomarkers of the present invention in the patient to obtain a post-treatment level of the one or more biomarkers; and
 d) comparing the pre-treatment and post-treatment biomarker levels to determine the efficacy of the treatment.

In one embodiment, the method comprises determining the level of two or more compounds selected from the group consisting of creatine riboside, metabolite 561+, cortisol sulfate and N-acetylneuraminic acid in the sample. In one embodiment, the method comprises determining the level of three or more compounds selected from the group consisting of creatine riboside, metabolite 561+, cortisol sulfate and N-acetylneuraminic acid in the sample. In one embodiment the method comprises determining the level of creatine riboside, metabolite 561+, cortisol sulfate and N-acetylneuraminic acid in the sample. In one embodiment, the cancer is lung cancer. In one embodiment, the cancer comprises adenocarcinoma. In one embodiment, the cancer comprises squamous cell carcinoma. In one embodiment, the sample is body tissue. In one embodiment, the sample is a body fluid. In one embodiment, the sample is urine. In one embodiment, the sample is selected from the group consisting of blood, serum and plasma.

One embodiment of the present invention is a method for predicting the prognosis of an individual having cancer, the method comprising determining the level of at least one biomarker selected from the group consisting of creatine riboside, cortisol sulfate, metabolite 561+ and N-acetylneuraminic acid, in a sample from the individual, wherein an elevated level of the at least one biomarker is indicative of the prognosis of the individual. In one embodiment, the method comprises determining the level of two or more compounds selected from the group consisting of creatine riboside, metabolite 561+, cortisol sulfate and N-acetylneuraminic acid in the sample. In one embodiment, the method comprises determining the level of three or more compounds selected from the group consisting of creatine riboside, metabolite 561+, cortisol sulfate and N-acetylneuraminic acid in the sample. In one embodiment the method comprises determining the level of creatine riboside, metabolite 561+, cortisol sulfate and N-acetylneuraminic acid in the sample. In one embodiment, the cancer is lung cancer. In one embodiment, the cancer comprises adenocarcinoma. In one embodiment, the cancer comprises squamous cell carcinoma. In one embodiment, the sample is body tissue. In one embodiment, the sample is a body fluid. In one embodiment, the sample is urine. In one embodiment, the sample is selected from the group consisting of blood, serum and plasma. In one embodiment, an elevated level of the at least one biomarker indicates a reduced survival time relative to a cancer patient in whom the level of the at least one biomarker is not elevated. In one embodiment, elevated levels of creatine riboside and metabolite 561+ indicate a reduced survival time relative to a cancer patient in whom the levels of creatine riboside and metabolite 561+ are not elevated. In one embodiment, elevated levels of creatine riboside, metabolite 561+, and N-acetylneuraminic acid indicate a reduced survival time relative to a cancer patient in whom the levels of creatine riboside, metabolite 561+ and N-acetylneuraminic acid are not elevated

BACKGROUND

Lung cancer is the leading cause of cancer deaths in men and women both in the United States (Jemal A, Simard E P, Dorell C, et al Annual Report to the Nation on the Status of Cancer, 1975-2009, Featuring the Burden and Trends in Human Papillomavirus (HPV)-Associated Cancers and HPV Vaccination Coverage Levels. J Natl Cancer Inst 2013; Jemal A, Bray F, Center M M, Ferlay J, Ward E, Forman D. Global cancer statistics. CA Cancer J Clin 2011; 61:69-90) and worldwide (Boyle P L B, ed. The World Cancer Report 2008. Lyon, France: IARC; 2008). Survival rates remain dismal, with 5-year survival ranging from <5% for distant, to 24% for regional, to 53% for localized disease (Horner M, Ries L A G, Krapcho M, et al. SEER Cancer Statistics Review, 1975-2006. In. Bethesda, Md.: National Cancer Institute; 2009). This substantial survival rate decrease in advanced disease provides a strong motivation to search for early diagnostic and prognostic biomarkers.

Current clinically accepted methods for the early detection of lung cancer are limited to spiral CT scanning in smokers between the ages of 55 to 74 and a 30 pack year smoking history (Jaklitsch M T, Jacobson F L, Austin J H, et al. The American Association for Thoracic Surgery guidelines for lung cancer screening using low-dose computed tomography scans for lung cancer survivors and other high-risk groups. J Thorac Cardiovasc Surg 2012; 144:33-8; American Cancer Society. American Cancer Society Guidelines for the Early Detection of Cancer, 2013. However, spiral CT scanning provides a high rate of false positives, namely 96.4% overall and 24% of those with invasive testing (Aberle D R, Adams A M, Berg C D, et al. Reduced lung-cancer mortality with low-dose computed tomographic screening. N Engl J Med 2011; 365:395-409). Also, spiral CT scanning may lead to an attendant increase in lung cancer risk due to radiation exposure (Brenner D J. Radiation risks potentially associated with low-dose CT screening of adult smokers for lung cancer. Radiology 2004; 231:440-5; Buls N, de Mey J, Covens P, Stadnik T. Health screening with CT: prospective assessment of radiation dose and associated detriment. JBR-BTR 2005; 88:12-6). Thus, a concordant biomarker to better identify those who should be screened or undergo invasive diagnostic work-ups is needed. Importantly, while imaging techniques perform poorly in identifying early stage lung cancer, the use of molecular biomarkers provides hope for early detection. However, to date, no molecular biomarker for early stage lung cancer has been validated (Vansteenkiste J, Dooms C, Mascaux C, Nackaerts K. Screening and early detection of lung cancer. Ann Oncol 2012; 23 Suppl 10:x320-7; Hassanein M, Callison J C, Callaway-Lane C, Aldrich M C, Grogan E L, Massion P P. The state of molecular biomarkers for the early detection of lung cancer. Cancer Prev Res (Phila) 2012; 5:992-1006).

Several biomarkers are available for the assessment of overall prognosis and for guiding therapy. For example, the KRAS mutation in non-small cell lung cancer (NSCLC) confers a significantly shorter survival (HR=1.21) in stage IV disease (Johnson M L, Sima C S, Chaft J, et al. Association of KRAS and EGFR mutations with survival in patients with advanced lung adenocarcinomas. Cancer 2013; 119:356-62). The presence of an ALK or EGFR mutation indicates a responsive tumor to targeted therapies and longer survival (Lynch T J, Bell D W, Sordella R, et al. Activating mutations in the epidermal growth factor receptor underlying responsiveness of non-small-cell lung cancer to gefitinib. N Engl J Med 2004; 350:2129-39; Paez J G, Janne P A, Lee J C, et al. EGFR mutations in lung cancer: correlation with clinical response to gefitinib therapy. Science 2004; 304:1497-500; Pao W, Miller V, Zakowski M, et al. EGF receptor gene mutations are common in lung cancers from "never smokers" and are associated with sensitivity of tumors to gefitinib and erlotinib. Proc Natl Acad Sci USA 2004; 101:13306-11; Mok T S, Wu Y L, Thongprasert S, et al. Gefitinib or carboplatin-paclitaxel in pulmonary adenocarcinoma. N Engl J Med 2009; 361:947-57; Antoniu S A. Crizotinib for EML4-ALK positive lung adenocarcinoma: a hope for the advanced disease? Evaluation of Kwak E L, Bang Y J, Camidge D R, et al. Anaplastic lymphoma kinase inhibition in non-small-cell lung cancer. N Engl J Med 2010; 363(18):1693-703. Expert Opin Ther Targets 2011; 15:351-3). However, current clinically accepted biomarkers for lung cancer outcomes are based on tumor assays, an invasive approach that can be limited due to tissue availability.

Urine is gaining increasing interest as a biospecimen for detecting cancer biomarkers (Schmidt C. Urine biomarkers may someday detect even distant tumors. J Natl Cancer Inst 2009; 101:8-10), notably because it is collected noninvasively, abundant, and requires minimal preparation. Presently, only one urinary cancer biomarker is clinically applied, PCA3, for detecting prostate cancer (Groskopf J, Aubin S M, Deras I L, et al. APTIMA PCA3 molecular urine test: development of a method to aid in the diagnosis of prostate cancer. Clin Chem 2006; 52:1089-95). However, no clinically applied biomarkers exist for lung cancer, but promising urinary biomarkers include modified nucleosides (Henneges C, Bullinger D, Fux R, et al. Prediction of breast cancer by profiling of urinary RNA metabolites using Support Vector Machine-based feature selection. BMC Cancer 2009; 9:104; Hsu W Y, Chen W T, Lin W D, et al. Analysis of urinary nucleosides as potential tumor markers in human colorectal cancer by high performance liquid chromatography/electrospray ionization tandem mass spectrometry. Clin Chim Acta 2009; 402:31-7; Jeng L B, Lo W Y, Hsu W Y, et al. Analysis of urinary nucleosides as helper tumor markers in hepatocellular carcinoma diagnosis. Rapid Commun Mass Spectrom 2009; 23:1543-9; Manjula S, Aroor A R, Raja A, Rao S, Rao A. Urinary excretion of pseudouridine in patients with brain tumours. Acta Oncol 1993; 32:311-4; Sasco A J, Rey F, Reynaud C, Bobin J Y, Clavel M, Niveleau A. Breast cancer prognostic significance of some modified urinary nucleosides. Cancer Lett 1996; 108:157-62; Vreken P, Tavenier P. Urinary excretion of six modified nucleosides by patients with breast carcinoma Ann Clin Biochem 1987; 24 (Pt 6):598-603; Xu G, Di Stefano C, Liebich H M, Zhang Y, Lu P. Reversed-phase high-performance liquid chromatographic investigation of urinary normal and modified nucleosides of cancer patients. J Chromatogr B Biomed Sci Appl 1999; 732:307-13; Xu G, Schmid H R, Lu X, Liebich H M, Lu P. Excretion pattern investigation of urinary normal and modified nucleosides of breast cancer patients by RP-HPLC and factor analysis method. Biomed Chromatogr 2000; 14:459-63), where high levels indicate an increased RNA turnover and degradation. Clinical trials evaluating the utility of these nucleotides in various diseases, including cancer, are ongoing.

Metabolomics is an increasingly popular approach for uncovering new biomarkers for diagnosis (Kim Y S, Maruvada P, Milner J A. Metabolomics in biomarker discovery: future uses for cancer prevention. Future Oncol 2008; 4:93-102; Kind T, Tolstikov V, Fiehn O, Weiss R H. A comprehensive urinary metabolomic approach for identifying kidney cancerr. Anal Biochem 2007; 363:185-95; Matsumura K, Opiekun M, Oka H, et al. Urinary volatile compounds as biomarkers for lung cancer: a proof of principle study using odor signatures in mouse models of lung cancer. PLoS One 2010; 5:e8819; Sreekumar A, Poisson L M, Rajendiran T M, et al. Metabolomic profiles delineate potential role for sarcosine in prostate cancer progression. Nature 2009; 457: 910-4; Yang Q, Shi X, Wang Y, et al. Urinary metabonomic study of lung cancer by a fully automatic hyphenated hydrophilic interaction/RPLC-MS system. J Sep Sci 2010; 33:1495-503; Yuan J M, Gao Y T, Murphy S E, et al. Urinary levels of cigarette smoke constituent metabolites are prospectively associated with lung cancer development in smokers. Cancer Res 2011; 71:6749-57) and customized treatment (Fan T W, Lane A N, Higashi R M. The promise of metabolomics in cancer molecular therapeutics. Curr Opin Mol Ther 2004; 6:584-92), and for evaluating characteristics of metastatic cells (Mountford C E, Wright L C, Holmes K T, Mackinnon W B, Gregory P, Fox R M. High-resolution proton nuclear magnetic resonance analysis of metastatic cancer cells. Science 1984; 226:1415-8) and carcinogenic tobacco-smoke constituents (Church T R, Anderson K E, Caporaso N E, et al. A prospectively measured serum biomarker for a tobacco-specific carcinogen and lung cancer in smokers. Cancer Epidemiol Biomarkers Prev 2009; 18:260-6; Hecht S S, Hatsukami D K, Bonilla L E, Hochalter J B. Quantitation of 4-oxo-4-(3-pyridyl)butanoic acid and enantiomers of 4-hydroxy-4-(3-pyridyl)butanoic acid in human urine: A substantial pathway of nicotine metabolism. Chem Res Toxicol 1999; 12:172-9; Hecht S S, Murphy S E, Stepanov I, Nelson H H, Yuan J M. Tobacco smoke biomarkers and cancer risk among male smokers in the Shanghai Cohort Study. Cancer Lett 201). However, most studies suffer from limited sample sizes, quality control, and lack of technical and biological validation. Metabolomic studies are unique and powerful because they measure both exogenous (e.g. cigarette smoke constituents) and endogenous molecules from cellular processes reacting to different types of exposures. Among methods for measuring metabolites, mass spectrometry is very sensitive and requires only small quantities of biospecimens (Griffin J L. The Cinderella story of metabolic profiling: does metabolomics get to go to the functional genomics ball? Philos Trans R Soc Lond B Biol Sci 2006; 361:147-61). A recent study has provided proof of principle evidence for the use of metabolomics in smokers that demonstrates the reliability and reproducibility of the assay, and the ability to distinguish levels and smoking status (Hsu P C, Zhou B, Zhao Y, et al. Feasibility of identifying the tobacco-related global metabolome in blood by UPLC-QTOF-MS. J Proteome Res 2012).

BRIEF DESCRIPTION OF THE FIGURES

FIG. 7. A) Creatine levels (quantitated abundances) are elevated in the tumors of the tissue sample set (48 matched tumor/adjacent non-tumor samples) B) Correlation analysis between creatine riboside and creatine quantitated in tumor tissue samples.

FIG. 17. Logistic regression analysis in liver cancer (Top) and prostate cancer (Bottom).

DETAILED DESCRIPTION OF THE INVENTION

Figure 2:
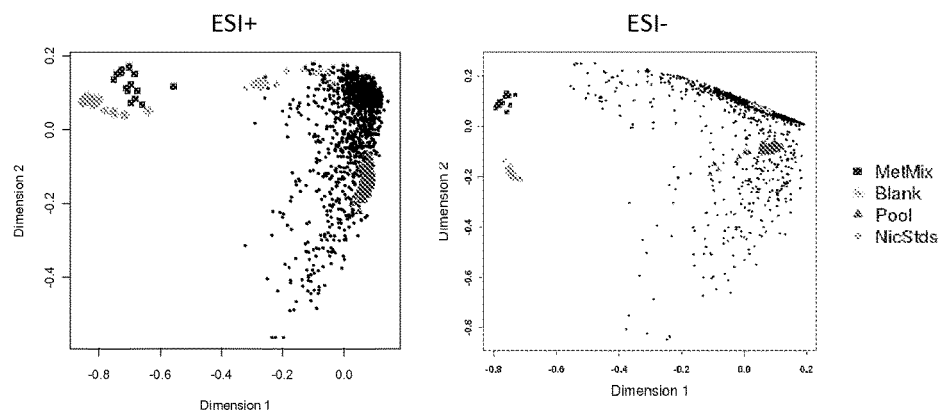
FIG. 2. Quality control assessment in the training set. A) Multidimensional scaling (1—Pearson's Correlation) as the distance metric was used for unsupervised clustering of ESI+ (left panel) and ESI− (right panel) data. Four controls were used to ensure the quality of the run: blanks (green asterisk), pooled samples (red triangles), MetMix mass spectrometry standards (blue squares), and nicotine metabolite standards diluted in water (orange diamonds). Urine collections from cancer patients and healthy controls are shown in black dots. B) Distribution of correlation coefficients in duplicate samples. Correlation coefficients were calculated between duplicate samples run in both ESI+(left) and ESI− (right) modes. Correlations were calculated before retention time alignment for duplicate samples (N=254 pairs) and for randomly selected pairs (N=2500 pairs). The distributions of these correlations show that duplicate samples have very similar metabolic profiles, as expected. C) Distribution of coefficients of variation (CVs) within each sample type demonstrates low CVs for the quality control samples when compared to lung cancer cases and healthy controls ($P<2E-6$).

Lung cancer remains the leading cause of cancer-related death in both men and women worldwide. The current clinically accepted method for early detection of lung cancer (i.e., spiral CT scanning) is expensive, exposes the patient to high levels of radiation and its use is limited to smokers within a certain age range. Moreover, current testing procedures result in a high rate of false positives. Thus, what is needed are methods for diagnosing cancer, and in particular lung cancer, that are less expensive, safer and more accurate. The present invention provides such methods. In particular, the present invention relates to a novel method for detecting cancer by detecting the level of specific biomarkers in an individual. Such a method is inexpensive, requires only a small sample from the patient and can be performed quickly and safely.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

A method of the present invention may generally be accomplished by determining the levels of one or more specific biomarkers, disclosed herein, within an individual, and determining if such levels are elevated compared to the levels of corresponding biomarkers in a sample from an individual known to be free of cancer. Determining the level of biomarkers of the present invention may also be referred to as determining the signature of the individual. As used herein, a signature refers to the levels of one or more cancer-related biomarkers of the present invention. The inventors have discovered that alterations of these levels relative to the levels of the same one or more biomarkers in individuals known to be free of cancer are indicative of the presence of cancer.

It should be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

As used herein, the terms individual, subject, patient, and the like, are meant to encompass any mammal capable of developing cancer, with a preferred mammal being a human. The terms individual, subject, and patient by themselves do not denote a particular age, sex, race, and the like. Thus, individuals of any age, whether male or female, are intended to be covered by the present disclosure. Likewise, the methods of the present invention can be applied to any race of human, including, for example, Caucasian (white), African-American (black), Native American, Native Hawaiian, Hispanic, Latino, Asian, and European. In some embodiments of the present invention, such characteristics may be significant. In such cases, the significant characteristic(s) (e.g., age, sex, race, etc.) will be indicated.

According to the present invention, the term individual encompasses both human and non-human animals. Suitable non-human animals to test for cancer include, but are not limited to companion animals (i.e. pets), food animals, work animals, or zoo animals. Preferred animals include, but are not limited to, cats, dogs, horses, ferrets and other Mustelids, cattle, sheep, swine, and rodents. More preferred animals include cats, dogs, horses and other companion animals, with cats, dogs and horses being even more preferred. As used herein, the term "companion animal" refers to any animal which a human regards as a pet. As used herein, a cat refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars, cheetahs, and servals. A preferred cat is a domestic cat. As used herein, a dog refers to any member of the family Canidae, including, but not limited to, domestic dogs, wild dogs, foxes, wolves, jackals, and coyotes and other members of the family Canidae. A preferred dog is a domestic dog. As used herein, a horse refers to any member of the family Equidae. An equid is a hoofed mammal and includes, but is not limited to, domestic horses and wild horses, such as, horses, asses, donkeys, and zebras. Preferred horses include domestic horses, including race horses.

The individual being tested may or may not be suspected of having cancer. It will be appreciated by those skilled in the art that some individuals are at higher risk than other individuals for developing cancer. For example, it is known that certain activities and environments increase the risk of developing cancer. Examples of such activities and environments included, but are not limited to smoking, exposure to second-hand smoke, exposure to asbestos, sun-tanning, exposure to radon gas, excessive alcohol consumption, exposure to high levels of radiation, and exposure to chemicals known to be carcinogenic. Thus, in one embodiment, the individual is known to engage in one or more activities that increases the risk for developing cancer. In one embodiment the individual has an increased risk of developing cancer.

Additionally, some individuals are at higher risk for developing cancer due to mutations in genes encoding proteins that act as tumor suppressor proteins. Mutations in these proteins render these proteins inefficient or ineffective resulting in the development of cancer. It is understood by those skilled in the art that a variant gene sequence may be referred to as an allele and that certain alleles are known to be associated with developing cancer. Examples of genes known to be associated with the development of cancer include, but are not limited to P53, APC, RB1, BRCA1, BRCA2, EGFR, KRAS, ALK, RET, KIT, and MET. In one embodiment, the individual carries a mutation or allele that is known to be associated with the development of cancer.

As used herein, cancer refers to diseases in which abnormal cells divide without the appropriate control of cell division and senescence. In some cancers, the cells are able to invade tissues other than those from which the original cancer cells arose. In some cancers, cancer cells may spread to other parts of the body through the blood and lymph systems. Thus, cancers are usually named for the organ or type of cell in which they start. For example, a cancer that originates in the colon is called colon cancer; cancer that originates in melanocytes of the skin is called melanoma, etc. As used herein, cancer may refer to carcinomas, sarcomas, adenocarcinomas, lymphomas, leukemias, etc., including solid and lymphoid cancers, gastric, kidney cancer, breast cancer, lung cancer (including non-small cell and small cell lung cancer), bladder cancer, colon cancer, ovarian cancer, prostate cancer, pancreas cancer, stomach cancer, brain cancer, head and neck cancers, skin cancer, uterine cancer, testicular cancer, esophageal cancer, liver cancer (including hepatocarcinoma), lymphoma, including non-Hodgkin's lymphomas (e.g., Burkitt's, Small Cell, and Large Cell lymphomas) and Hodgkin's lymphoma, leukemia, and multiple myeloma. In one embodiment, the cancer is lung cancer. In one embodiment, the cancer is adenocarcinoma.

Figure 1:
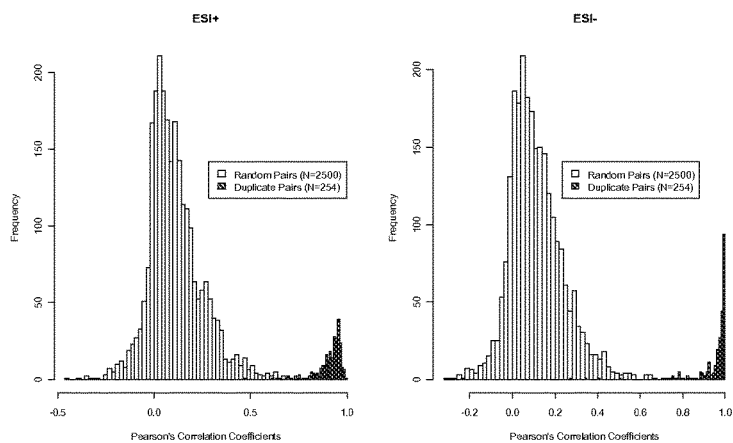
FIG. 1. Lung cancer staging staging system. (A) Definitions used to stage tumors. (B) Anatomic stage and prognostic groups.
Figure 2:
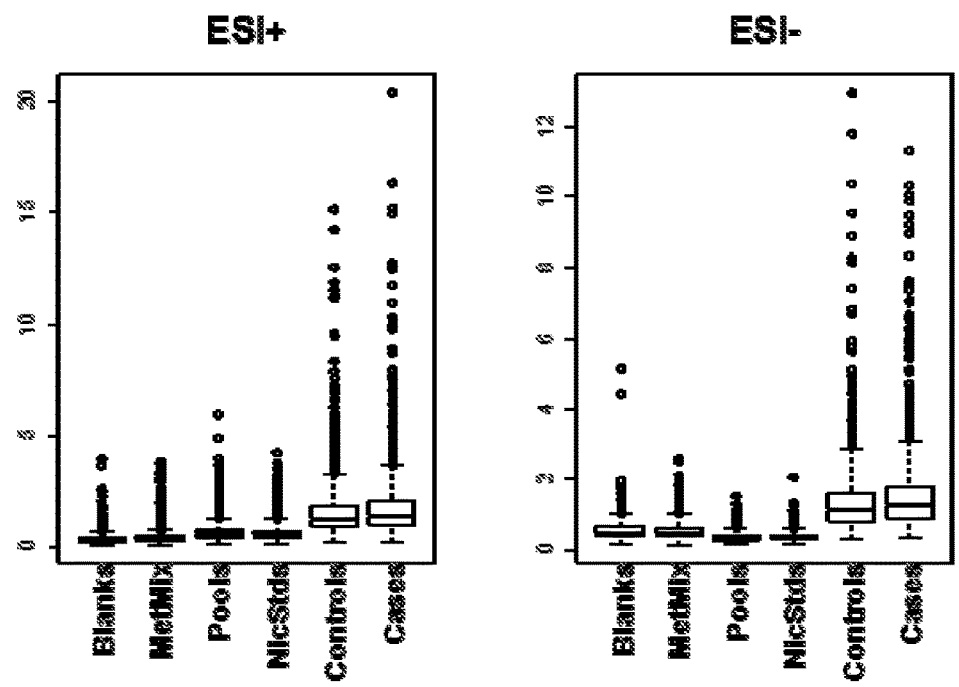

It is understood in the art that early detection of cancer is important in order to improve the odds of survival. For example, with regard to lung cancer, the 5 year survival rate is 50% when the disease is caught in the early stages. Staging of a cancer is a classification system based on such things as the involvement of lymph nodes and metastasis of the tumor to secondary sites. For example, a new tumor starts out in Stage 0 but as it grows and spreads it progresses through Stages 1-IV. One Example of a staging system is shown in FIGS. 1A and 1B. With regard to the present invention, staging of the cancers disclosed herein was performed according to the method of Edge S., et al., AJCC Cancer Staging Manual. $7^{th}$ ed: Springer-Verlag; 2010, which is incorporated in it's entirety. As used herein, early stages of cancer, early cancer, early disease, and the like, refer to a cancer that is in Stage 0, Stage I or Stage II. In one embodiment, the individual being tested is suspected of being in the early stages of cancer.

A biomarker may be described as a characteristic that is objectively measured and evaluated as an indicator of normal biologic processes, pathogenic processes, or pharmacologic responses to a therapeutic intervention (Biomarkers Definitions Working Group. Biomarkers and surrogate endpoints: preferred definitions and conceptual framework. Clin Pharmacol Ther. 2001 March; 69(3):89-95.) As used herein, the terms biomarker, cancer-marker, cancer-associated biomarker, cancer-associated antigen, and the like, refer to a molecule, the level of which is altered in an individual having cancer relative to the level of the same biomarker in an individual known to be free of cancer. A cancer biomarker may be any molecule for which the level of the molecule in an individual having cancer is altered in comparison to the level observed in an individual free of cancer. Examples of such molecules include nucleic acid molecules (i.e., RNA and DNA), proteins, lipids, carbohydrates, amino acids, nucleotides and combinations thereof. Preferred biomarkers are those for which the levels of the biomarker may be determined in a quick and efficient manner.

With regard to the biomarkers disclosed herein, the inventors have discovered that the levels of one or more such biomarkers are elevated (i.e., increased) in individuals having cancer. As used herein, the term elevated refers to an increased level of a biomarker in an individual having cancer compared to the level of biomarker observed in an individual known to be free of cancer (the normal level). According to the present invention, the normal level of a biomarker is the level observed in a) a population of individuals known to be free of cancer; and/or 2) the level of biomarker observed in the individual being tested, wherein the level was determined at a time when the individual was known to be free of cancer. A normal level may also be referred to as a base level, control level or reference level.

In one embodiment, the level of at least one biomarker in an individual having cancer is at least 1.2-fold, at least 1.4-fold, at least 1.6-fold, at least 1.8-fold, at least 2-fold, at least 3-fold, at least 4-fold, at least 5-fold, at least 10-fold, at least 15-fold, at least 20-fold, at least 25-fold, at least 50-fold or at least 100-fold greater than the normal level of the at least one biomarker. In one embodiment, the level of at least one biomarker in an individual having cancer is elevated by at least 20%, at least 30%, at least 40%, at least 50%, at least 100%, at least 200%, at least 300%, at least 400%, at least 500% at least 1000%, at least 2000%, at least 5000% or at least 10,000% over the normal level of the at least one biomarker.

The present inventors have discovered that elevated levels of specific biomarkers, either alone or in combination, may be used to identify individuals having cancer. Thus, one embodiment of the present invention is a method for identifying an individual having cancer, comprising determining the level of at least two biomarkers of the present invention, wherein elevated levels of the at least two biomarkers indicates the presence of cancer. Examples of useful biomarkers for identifying individuals having cancer include, but are not limited to, creatine riboside, metabolite 561+, cortisol sulfate and N-acetylneuraminic acid (NANA).

The structures of N-acetylneuraminic acid and cortisol sulfate are shown below and are also described in the database and ontology of Chemical Entities of Biological Interest (ChEBI) of the European Bioinformatics Institute (EBI), which is part of the European Molecular Biology Laboratory.

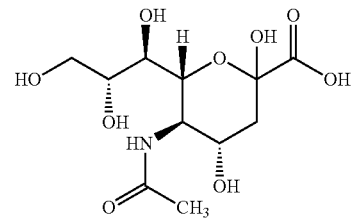
N-acetylneuraminic acid

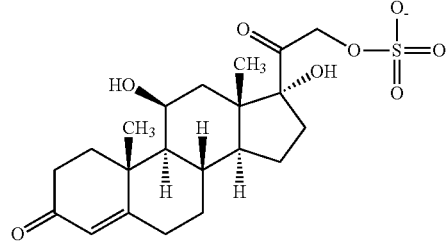
Cortisol sulfate

Creatine riboside (formula=C9H17N3O6) is a novel compound, the structure of which is shown in FIG. 5E. In particular, FIG. 5E shows the product ion mass spectra obtained by monitoring characteristic fragmentation patterns in multiple reaction monitoring (MRM) mode. The chemical structures illustrated in FIG. 5E were determined according to the methods disclosed in Example 1.

Metabolite 561+ is a glucoronidated lipid, the MS-MS fragmentation patterns of which are shown in FIG. 5D. The chemical and physical characteristics of compound 561+ were determined as described in Example 1.

One embodiment of the present invention is a method for detecting the presence of cancer in an individual, comprising determining the level of at least two biomarkers selected from the group consisting of creatine riboside, metabolite 561+, cortisol sulfate and N-acetylneuraminic acid, wherein elevated levels of the at least two biomarkers indicates the presence of cancer. In some embodiments, assays using additional biomarkers may lead to improved rates of detection and diagnosis of cancer. Thus, one embodiment is a method for detecting the presence of cancer in an individual, comprising determining the level of at least three biomarkers selected from the group consisting of creatine riboside, metabolite 561+, cortisol sulfate and N-acetylneuraminic acid, wherein elevated levels of the at least three biomarkers indicates the presence of cancer. One embodiment is a method for detecting the presence of cancer in an individual, comprising determining the level of creatine riboside, metabolite 561+, cortisol sulfate and N-acetylneuraminic acid, wherein elevated levels creatine riboside, metabolite 561+, cortisol sulfate and N-acetylneuraminic acid indicates the presence of cancer. In one embodiment, the cancer is colon cancer. In one embodiment, the cancer is lung cancer. In one embodiment the cancer is adenocarcinoma. In one embodiment, the cancer is squamous cell carcinoma.

In one embodiment of the present invention, the level of one or more biomarkers is determined from a sample obtained, or collected, from an individual to be tested for the presence of cancer. A sample is any specimen obtained from the individual that can be used to measure the level one or more biomarkers. In a particular embodiment, a sample is any specimen obtained from the individual that can be used to measure the level one or more biomarkers selected from the group consisting of creatine riboside, metabolite 561+, cortisol sulfate and N-acetylneuraminic acid. Examples of useful samples include body fluids and tissue from an individual being tested. A preferred sample is a bodily fluid. Those skilled in the art can readily identify appropriate types of samples.

Urine, blood plasma and blood serum are particularly suitable as the sample. Blood plasma ("plasma") or blood serum ("serum") may be obtained using standard techniques know to those skilled in the art. Urine samples may also be collected from animals by methods known in the art, including, for example, collecting while the individual is voiding, collecting by catheterization, or by cystocentesis. Urine, plasma, or serum samples may be refrigerated or frozen before assay, but are preferably assayed soon after collection. In one embodiment, the level of one or more biomarkers is determined from a plasma or serum sample. In one embodiment, the level of one or more biomarkers is determined from a urine sample.

Although not necessary for the present invention, the sample may be pre-treated as desired prior to determining the level of biomarkers present in the sample. For example, the sample can be filtered, treated chemically or enzymatically or, if the sample is urine, it may be normalized to a desired specific gravity. Normalizing the sample by appropriate dilution methods known in the art permits quantification of biomarkers independent of the concentration (e.g. specific gravity) of the sample. Any desired specific gravity can be readily selected by those skilled in the art. Additionally, the level of a biomarker present in a sample may be normalized to another compound present in the sample, such as, for example, hemoglobin level, packed red cell volume or creatinine Appropriate methods for normalizing a sample are known to those skilled in the art.

As has been discussed, methods of the present invention rely on determining the level of biomarkers. As used herein, the terms "determine," "determine the level of a biomarker," "determine the amount of a biomarker," "determine the biomarker level," and the like are meant to encompass any technique which can be used to detect or measure the presence or level of one or more biomarkers. Such techniques may give qualitative or quantitative results. Biomarker levels can be determined by detecting the entire biomarker molecule or by detecting fragments, degradation products or reaction products that are characteristic of the biomarker molecule. The terms determining, measuring or taking a measurement refer to a quantitative or qualitative determination of a property of an entity, for example, quantifying the amount or concentration of a molecule or the activity level of a molecule. The term concentration or level can refer to an absolute or relative quantity. For example, the level of a biomarker may be reported as a concentration (e.g., ug/ml), it may be reported relative to another value such as a normal value (e.g., 3-fold higher than normal), or it may be reported as a ratio relative to a second molecule (e.g., a biomarker/creatinine ratio of 1.6). Measuring a molecule may also include determining the absence or presence of the molecule in a sample.

Any known method of detecting or measuring the level of a biomarker can be used to practice the present invention, so long as the method detects the presence, absence, or level or concentration of the biomarker. Examples of such methods include, but are not limited to, binding assays, such as an immunological detection assays and non-binding assays (e.g., enzymatic detection assays or assays that detect physical characteristics such as mass).

In a binding assay, the sample to be tested for the presence, absence or level of a biomarker is contacted with a binding molecule such as, for example, an antibody. As used herein, the term contact, contacted, contacting, and the like, refers to the introduction of a sample putatively containing a biomarker to a compound that binds to the biomarker. One example of a biomarker-binding compound is an antibody that selectively binds to the biomarker. However, other molecules that bind to the biomarker may also be used. For example, if the biomarker is a ligand, a receptor to which ligand binds can be used as a biomarker-binding compound in assays of the present invention. Appropriate binding molecules for the biomarkers disclosed herein may be determined by those skilled in the art.

In a binding assay, such as an immunological assay, when a biomarker is present in the sample, a biomarker-binding compound complex is formed. Such complex formation refers to the ability of a biomarker-binding compound to selectively bind to the biomarker in order to form a stable complex that can be detected. As used herein, the terms selectively, selective, specific, and the like, indicate the biomarker-binding compound has a greater affinity for the biomarker than it does for molecules that are unrelated to the biomarker. More specifically, the terms selectively, selective, specific, and the like indicate that the affinity of the biomarker-binding compound for a biomarker is statistically significantly higher than its affinity for a negative control (e.g., an unrelated molecule, such as, for example, albumin) as measured using a standard assay (e.g., ELISA). Detection of the complex can be qualitative, quantitative, or semi-quantitative. Conditions for allowing selective binding and complex formation (e.g., appropriate concentrations, buffers, temperatures, reaction times) as well as methods to optimize such conditions are known to those skilled in the art. Binding can be measured using a variety of methods standard in the art including, but not limited to, enzyme immunoassays (e.g., ELISA), immunoprecipitations, immunoblot assays and other immunoassays as described, for example, in Sambrook et al., supra, and Harlow, et al., supra. These references also provide examples of complex formation conditions.

In one embodiment, the biomarker/binding-compound complex also referred to herein as the B/BC complex or simply as the complex, can be formed in solution. In another embodiment, the complex can be formed while the biomarker-binding compound is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (polyvinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a sponge, a cotton thread, a plastic chip, an immunoblot membrane, an immunoblot paper and a flow-through membrane. In one embodiment, a substrate, such as a particulate, can include a detectable marker. For descriptions of examples of substrate materials, see, for example, Kemeny, D. M. (1991) A Practical Guide to ELISA, Pergamon Press, Elmsford, N.Y. pp 33-44, and Price, C. and Newman, D. eds. Principles and Practice of Immunoassay, 2nd edition (1997) Stockton Press, NY, N.Y., both of which are incorporated herein by reference in their entirety.

In one embodiment, a biomarker-binding compound is immobilized on a substrate, such as the well of a microtiter dish, a dipstick, an immunodot strip, or a lateral flow apparatus. A sample collected from an individual is applied to the substrate and incubated under conditions suitable (i.e., sufficient) to allow the formation of a complex between the binding compound and any biomarker present in the sample.

In accordance with the present invention, once formed, the complex is then detected. As used herein, the terms "detecting the complex", "detecting complex formation" and the like refer to identifying the presence of biomarker-binding compound complexed to a biomarker of the present invention. If complexes are formed, the amount of complexes formed can, but need not be, quantified. Complex formation, or selective binding between a biomarker and a biomarker-binding compound, can be measured (i.e., detected, determined) using a variety of methods standard in the art (see, for example, Sambrook et al. supra.), examples of which are disclosed herein. A complex can be detected in a variety of ways including, but not limited to use of one or more of the following assays: an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BIACORE™ assay (e.g., using colloidal gold), an immunodot assay (e.g., CMG's Immunodot System, Fribourg, Switzerland), and an immunoblot assay (e.g., a western blot), an phosphorescence assay, a flow-through assay, a chromatography assay, a PAGE-based assay, a surface plasmon resonance assay, a spectrophotometric assay, a particulate-based assay, and an electronic sensory assay. Such assays are well known to those skilled in the art. Some assays, such as agglutination, particulate separation, and immunoprecipitation, can be observed visually (e.g., either by eye or by a machines, such as a densitometer or spectrophotometer) without the need for a detectable marker.

In other assays, conjugation (i.e., attachment) of a detectable marker to the biomarker-binding compound or to a reagent that selectively binds to the biomarker-binding compound aids in detecting complex formation. A detectable marker may be conjugated to the biomarker-binding compound, or reagent, at a site that does not interfere with ability of the compound to bind the biomarker. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

Means of detecting such markers are well known to those of skill in the art. Thus, for example, radiolabels may be detected using photographic film or scintillation counters; fluorescent markers may be detected using a photodetector to detect emitted light. Enzymatic markers are typically detected by providing the enzyme with a substrate and detecting the reaction product produced by the action of the enzyme on the substrate, and colorimetric markers are detected by simply visualizing the colored label.

In one embodiment, a biomarker/binding compound complex can be detected by contacting a sample with an antibody specific for the binding compound, wherein the antibody is conjugated to a detectable marker. A detectable marker can also be conjugated to an anti-biomarker antibody, or other binding compound. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

In another embodiment, a complex is detected by contacting the complex with an indicator molecule. Suitable indicator molecules include molecules that can bind to the B/BC complex or to the biomarker itself. As such, an indicator molecule can comprise, for example, a biomarker-binding reagent, such as an antibody. Examples of indicator molecules that are antibodies include, for example, antibodies reactive with the antibodies from species of animal in which the anti-biomarker antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

One embodiment of the present invention involves the use of a lateral flow assay, examples of which are described in U.S. Pat. No. 5,424,193, issued Jun. 13, 1995, to Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; all of which are incorporated by reference herein. A lateral flow assay is an example of a single-step assay. In a single-step assay, once the sample has been obtained and made ready for testing, only a single action is necessary on the part of the user to detect the present of an analyte. For example, the sample, in whole or part, can be applied to a device that measures analyte in the sample. In one embodiment, a sample is placed in a lateral flow apparatus that includes the following components: (a) a support structure defining a flow path; (b) a labeling reagent comprising a bead conjugated to a specific antibody, the labeling reagent being impregnated within the support structure in a labeling zone; and (c) a capture reagent. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose, PVDF, or carboxymethylcellulose. The support structure defines a flow path that is lateral and is divided into zones, namely a labeling zone and a capture zone. The apparatus can further include a sample receiving zone located along the flow path, preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In another embodiment, a lateral flow apparatus used to detect a biomarker includes: (a) a support structure defining a flow path; (b) a labeling reagent comprising an anti-biomarker antibody as described above, the labeling reagent impregnated within the support structure in a labeling zone; and (c) a capture reagent, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path. One preferred embodiment includes a capture reagent comprising a biomarker binding compound.

One embodiment of the present invention is a "dipstick" device that can detect biomarkers in individuals. Dipsticks may be constructed in a variety of ways that partly depend on the way in which they will be used. They may be held directly in a sample (e.g., a urine stream), dipped directly in sample contained in a collection vessel, or have sample applied to a strip contained in a plastic cassette or platform. Another example of a dipstick is a "flow-through" device, an example of which is a heterogenous immunometric assay system based on a capture antibody immobilized onto a membrane attached to an absorbent reservoir, A "bead" refers to a particulate substrate composed of a matrix such as latex or polystyrene, which can be covalently or non-covalently cross-linked to a detection molecule. A preferred embodiment of the "dipstick" assay is an immunometric system, described in U.S. Pat. No. 5,656,502, issued on Aug. 12, 1997, to MacKay and Fredrickson, and U.S. Pat. No. 6,001,658, issued Dec. 14, 1999 to Fredrickson, both incorporated herein by reference. Particularly preferred is an IMMUNODIP™ device available from Diagnostic Chemicals Ltd., PEI, Calif.

In addition to the immunological methods described above, various methods of detecting and/or determining the level of a biomarker include, but are not limited to, refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Once the level of a biomarker has been determined, the level may be compared to the normal level of the same biomarker and a determination of whether or not the individual has cancer can be made. As previously described, elevated levels of one or more of the biomarkers disclosed herein indicate the individual has cancer. In one embodiment, an elevated level of at least two compounds selected from the group consisting of creatine riboside, metabolite 561+, cortisol sulfate and N-acetylneuraminic acid in a sample obtained from the individual, indicates the presence of cancer. Comparison of the level of biomarker in the individual being tested to the normal level may be performed by any method that allows the detection of the level of a biomarker. For example, if immunoassays (e.g., ELISA) are used to determine levels of a biomarker, a corresponding immunoassay may be performed using a sample from a normal individual and the numeric results from the assays compared. Assay of the normal sample may be performed at the same time as the test sample or it may be performed prior to, or after, the level of biomarker in the test sample is determined. Biomarkers levels from the individual being tested can also be compared to a historical normal value, which is a value obtained from one or more cancer-free individuals over time. Comparison of the results may be performed visually or they may be performed by a machine (e.g., computer). Further, if the results are performed by machine, the output of such comparison may be a numeric value, such as the difference between values, or it may be a qualitative result, such as a yes or no with regard to the presence of cancer. Similar methods of comparison may be performed using any of the detection methods disclosed herein (e.g., mass spectrometry).

In certain embodiments, the number of biomarkers chosen for measurement, and the sample used to determine the level of the biomarker will vary. For example, in some instances, determination of the level of a single biomarker is sufficient for the detection of cancer. Examples of useful, single biomarkers include, but are not limited to, creatine riboside and N-acetylneuraminic acid (NANA). Thus, one embodiment of the present invention is a method to detect the presence of cancer in an individual, the method comprising determining the level of one or more biomarkers selected from the group consisting of creatine riboside and NANA in a sample from the individual, wherein elevated levels of creatine riboside or NANA indicates the presence of cancer in the individual. In one embodiment, the biomarker being measured is creatine riboside. In one embodiment, the biomarker being measured is NANA. In one embodiment, the level of biomarker is determined from a tissue sample. In one embodiment, the level of biomarker is determined from at least one body fluid selected from the group consisting of plasma, serum and urine. In one embodiment, the body fluid is urine. In one embodiment the cancer is colon cancer. In one embodiment, the cancer is lung cancer. In one embodiment, the cancer is adenocarcinoma.

In other embodiments, the choice of biomarker, and the number of biomarkers measured, may depend on the type of cancer for which the individual is being screened. For example, the inventors have demonstrated that elevated levels of cortisol sulfate in some body fluids are indicative of the presence of lung cancer. Thus, one embodiment of the present invention is a method to detect the presence of lung cancer in an individual, the method comprising determining the level of cortisol sulfate in body fluid obtained from the individual, wherein elevated levels of cortisol sulfate indicates the presence of cancer in the individual. In one embodiment, the body fluid may be plasma, serum or urine. In one embodiment, the cancer is adenocarcinoma. In one embodiment, the cancer is squamous cell carcinoma.

In certain embodiments, elevated levels of a specific biomarker in a particular bodily fluid are indicative of the presence of specific types of cancers. For example, the inventors have discovered that elevated levels of N-acetylneuraminic acid in the urine are indicative of lung cancer. Thus, one embodiment of the present invention is a method to detect the presence of cancer in an individual, the method comprising determining the level of N-acetylneuraminic acid in urine from the individual, wherein elevated levels of urinary N-acetylneuraminic acid indicates the presence of lung cancer in the individual. In one embodiment the cancer is an adenocarcinoma. In one embodiment, the cancer is squamous cell carcinoma.

Because the levels of biomarkers of the present invention may be used to detect cancer, they may therefore be used to identify individuals having cancer. Thus, one embodiment of the present invention is a method for identifying an individual having cancer, the method comprising determining the level of at least two biomarkers in a body fluid obtained from an individual, wherein the at least two biomarkers are selected from the group consisting of creatine riboside, metabolite 561+, cortisol sulfate and N-acetylneuraminic acid, and wherein elevated levels of the at least two biomarkers identifies the individual as having cancer. One embodiment of the present invention is a method for identifying an individual having cancer, the method comprising determining the level of at least three biomarkers in a body fluid obtained from an individual, wherein the at least three biomarkers are selected from the group consisting of creatine riboside, metabolite 561+, cortisol sulfate and N-acetylneuraminic acid, and wherein elevated levels of the at least three biomarkers identifies the individual as having cancer. One embodiment is a method for identifying an individual having cancer, comprising determining the level of creatine riboside, metabolite 561+, cortisol sulfate and N-acetylneuraminic acid, wherein elevated levels creatine riboside, metabolite 561+, cortisol sulfate and N-acetylneuraminic acid identify the individual as having cancer. One embodiment of the present invention is a method to identify an individual having cancer, the method comprising determining the level of one or more biomarkers selected from the group consisting of creatine riboside and NANA, wherein elevated levels of creatine riboside and/or NANA identifies the individual as having cancer. In one embodiment the cancer is colon cancer. In one embodiment the cancer is lung cancer. In one embodiment the cancer is adenocarcinoma. In one embodiment the cancer is squamous cell carcinoma.

One embodiment of the present invention is a method to identify an individual having lung cancer, the method comprising determining the level of cortisol sulfate in a body fluid obtained from an individual, wherein elevated levels of cortisol sulfate identify the individual as having lung cancer. One embodiment of the present invention is a method to identify an individual having lung cancer, the method comprising determining the level of N-acetylneuraminic acid in urine obtained from an individual, wherein elevated levels of urinary N-acetylneuraminic acid identifies the individual as having lung cancer.

If an individual has been identified as having cancer, that individual may also be identified as being in need of treatment for cancer. As used herein, a treatment or therapy for cancer refers to any treatment or therapy that is intended to reduce the cancer load or prevent the cancer load from increasing. Examples of treatments include, but are not limited to, surgery, chemotherapy, biotherapy and radiation. According to the present invention, the term cancer load may refer to the mass, size or number of cancer cells present in a patient. Thus, for example, if the pre-treatment and post-treatment biomarker levels remain substantially unchanged, this would indicate that the treatment is preventing an increase in cancer load. If the difference between the pre-treatment and post-treatment biomarker levels decrease, this is an indication that the treatment is reducing the cancer load. In one embodiment, the at least two biomarkers are selected from the group consisting of creatine riboside, metabolite 561+, cortisol sulfate and N-acetylneuraminic acid. In one embodiment, the level of at least three biomarkers are determined, wherein the biomarkers are selected from the group consisting of creatine riboside, metabolite 561+, cortisol sulfate and N-acetylneuraminic acid. In one embodiment, the level of creatine riboside, metabolite 561+, cortisol sulfate and N-acetylneuraminic acid are detected.

Methods disclosed herein may be used to monitor the efficacy of a cancer treatment. For example, in patients undergoing treatment for cancer, it is desirable for tumor size to be diminished and, eventually, for the patient to be free of cancer. Consequently, the levels of tumor-specific biomarkers should also return to normal. Thus, one embodiment of the present invention is a method for monitoring the efficacy of a cancer treatment, the method comprising:

a) determining the level of one or more biomarkers of the present invention in a patient having cancer to obtain a pre-treatment level of the one or more biomarkers;

b) administering a cancer treatment to the patient;

c) at a period of time following administration of the treatment, determining the level of the one or more biomarkers of the present invention in the patient to obtain a post-treatment level of the one or more biomarkers; and d) comparing the pre-treatment and post-treatment biomarker levels to determine the efficacy of the treatment. In one embodiment, efficacy of treatment for cancer is monitored by determining the level of one or more biomarkers selected from the group consisting of creatine riboside and N-acetylneuraminic acid (NANA). In one embodiment, efficacy of treatment for cancer is monitored by determining the level of at least two biomarkers selected from the group consisting of creatine riboside, metabolite 561+, cortisol sulfate and N-acetylneuraminic acid in body fluid obtained from the individual. In one embodiment, efficacy of treatment for lung cancer is monitored by determining the level of cortisol sulfate in a sample of body fluid from the individual. In one embodiment, efficacy of treatment for lung cancer is monitored by determining the level of N-acetylneuraminic acid in urine from the individual.

The inventors have also discovered that the levels of certain biomarkers of the present invention are useful for predicting the prognosis of a patient having cancer. In particular, the inventors have discovered that the levels of creatine riboside and metabolite 561+ are related to the prognosis of a patient having cancer. Thus, one embodiment of the present invention is a method for predicting the prognosis of an individual having cancer, the method comprising determining the level of at least one biomarker selected from the group consisting of creatine riboside and metabolite 561+, wherein an elevated level of the at least one biomarker is indicative of the prognosis of the individual. In one embodiment, the levels of creatine riboside and metabolite 561+ are determined. In a particular embodiment, the at least one biomarker level is determined when the cancer is in an early stage. In one embodiment, an elevated level of the at least one biomarker indicates a reduced survival time relative to a cancer patient in whom the level of the at least one biomarker is not elevated. In one embodiment, elevated levels of creatine riboside and metabolite 561+ indicate a reduced survival time relative to a cancer patient in whom the levels of creatine riboside and metabolite 561+ are not elevated.

It should be appreciated that the diagnostic and prognostic accuracy of biomarkers of the present invention may be improved when the levels of such biomarkers are measured in combination with the level or presence of other, known cancer biomarkers. The known biomarker may be any molecule for which an association between the level or presence of the molecule and a diagnosis of cancer (or a prognosis related thereto) has been established. Examples of known biomarkers to measure include, but are not limited to, proteins, nucleic acid molecules, lipids, carbohydrates and combinations thereof. One type of known biomarker to measure in combination with one or more biomarker of the present invention is a microRNA (miRNA). MicroRNAs are small, non-coding RNAs, that have been shown to regulate epigenetic phenomena (Lee, R C, Feinbaum R L, Ambros, V. The *C. elegans* heterochronic gene lin-4 encodes small RNAs with antisense complimentarity to lin-14. Cell 993; 75(5):843-54). These small RNA molecules, which are usually 18-25 nucleotides in size, repress the translation of target genes by complimentary binding to their 3'UTR sequence (Carthew, R W, Sontheimer E J. Origins and Mechanisms of miRNAs and siRNAs. Cell 2009; 136(4): 642-55). Since their discovery, miR-mediated post-transcriptional modulation of gene expression has been found to be associated with a number of diseases, including cancer (Yang B, Lin H, Xiao J, et al. The muscle-specific microRNA miR-1 regulates cardiac arrhythmogenic potential by targeting GJA1 and KCNJ2. Nat Med 2007; 13(4):486-91; Saito M, Schetter A J, Mollerup S, et al. The association of microRNA expression with prognosis and progression in early-stage, non-small cell lung adenocarcinoma: a retrospective analysis of three cohorts. Clin Cancer Res 2011; 17(7):1875-82; Park J K, Lee E J, Esau C, et al. Antisense inhibition of microRNA-21 or -221 arrests cell cycle, induces apoptosis, and sensitizes the effects of gemcitabine in pancreatic adenocarcinoma. Pancreas 2009; 38(7):e190-9; Markou A, Tsaroucha E G, Kaklamanis L, et al. Prognostic value of mature microRNA-21 and microRNA-205 overexpression in non-small cell lung cancer by quantitative real-time R T-PCR. Clin Chem 2008; 54(10):1696-704; Esau C, Davis S, Murray S F, et al. miR-122 regulation of lipid metabolism revealed by in vivo antisense targeting. Cell Metab 2006; 3(2):87-98; Bakirtzi K, Hatziapostolou M, Karagiannides I, et al. Neurotensin signaling activates microRNAs-21 and -155 and Akt, promotes tumor growth in mice, and is increased in human colon tumors. Gastroenterology 2011; 141(5):1749-61 el; Asangani I A, Rasheed S A, Nikolova D A, et al. MicroRNA-21 (miR-21) post-transcriptionally downregulates tumor suppressor Pdcd4 and stimulates invasion, intravasation and metastasis in colorectal cancer. Oncogene 2008; 27(15):2128-36) In fact, a number of miRs have been found to be deregulated in several types of cancers (Park J K, Lee E J, Esau C, et al. Antisense inhibition of microRNA-21 or -221 arrests cell cycle, induces apoptosis, and sensitizes the effects of gemcitabine in pancreatic adenocarcinoma. Pancreas 2009; 38(7):e190-9; Bakirtzi K, Hatziapostolou M, Karagiannides I, et al. Neurotensin signaling activates microRNAs-21 and -155 and Akt, promotes tumor growth in mice, and is increased in human colon tumors. Gastroenterology 2011; 141(5):1749-61 el; Asangani I A, Rasheed S A, Nikolova D A, et al. MicroRNA-21 (miR-21) post-transcriptionally downregulates tumor suppressor Pdcd4 and stimulates invasion, intravasation and metastasis in colorectal cancer. Oncogene 2008; 27(15):2128-36; Papagiannakopoulos T, Shapiro A, Kosik K S. MicroRNA-21 targets a network of key tumor-suppressive pathways in glioblastoma cells. Cancer Res 2008; 68(19):8164-72; Meng F, Henson R, Wehbe-Janek H, et al. MicroRNA-21 regulates expression of the PTEN tumor suppressor gene in human hepatocellular cancer. Gastroenterology 2007; 133(2):647-58; Volinia S, Calin G A, Liu C G, et al. A microRNA expression signature of human solid tumors defines cancer gene targets. Proc Natl Acad Sci USA 2006; 103(7):2257-61; Takahashi Y, Forrest A R, Maeno E, et al. MiR-107 and MiR-185 can induce cell cycle arrest in human non small cell lung cancer cell lines. PLoS One 2009; 4(8):e6677). For example, mir-21 has been found to be up-regulated in most cancer sites, including lung, pancreas, liver and colon (Saito M, Schetter A J, Mollerup S, et al. The association of microRNA expression with prognosis and progression in early-stage, non-small cell lung adenocarcinoma: a retrospective analysis of three cohorts. Clin Cancer Res 2011; 17(7):1875-82; Park J K, Lee E J, Esau C, et al. Antisense inhibition of microRNA-21 or -221 arrests cell cycle, induces apoptosis, and sensitizes the effects of gemcitabine in pancreatic adenocarcinoma. Pancreas 2009; 38(7):e190-9; Markou A, Tsaroucha E G, Kaklamanis L, et al. Prognostic value of mature microRNA-21 and microRNA-205 overexpression in non-small cell lung cancer by quantitative real-time R T-PCR. Clin Chem 2008; 54(10):1696-704; Asangani I A, Rasheed S A, Nikolova D A, et al. MicroRNA-21 (miR-21) post-transcriptionally downregulates tumor suppressor Pdcd4 and stimulates invasion, intravasation and metastasis in colorectal cancer. Oncogene 2008; 27(15):2128-36; Meng F, Henson R, Wehbe-Janek H, et al. MicroRNA-21 regulates expression of the PTEN tumor suppressor gene in human hepatocellular cancer. Gastroenterology 2007; 133(2):647-58). An increase in miR-21 expression has been associated with poor prognosis in lung cancer patients (Saito M, Schetter A J, Mollerup S, et al. The association of microRNA expression with prognosis and progression in early-stage, non-small cell lung adenocarcinoma: a retrospective analysis of three cohorts. Clin Cancer Res 2011; 17(7):1875-82; Markou A, Tsaroucha E G, Kaklamanis L, et al. Prognostic value of mature microRNA-21 and microRNA-205 overexpression in non-small cell lung cancer by quantitative real-time R T-PCR. Clin Chem 2008; 54(10):1696-704; Akagi I, Okayama H, Schetter A J, et al. Combination of Protein Coding and Noncoding Gene Expression as a Robust Prognostic Classifier in Stage I Lung Adenocarcinoma. Cancer Res 2013), and is believed to promote tumor invasiveness and metastasis (Asangani I A, Rasheed S A, Nikolova D A, et al. MicroRNA-21 (miR-21) post-transcriptionally downregulates tumor suppressor Pdcd4 and stimulates invasion, intravasation and metastasis in colorectal cancer. Oncogene 2008; 27(15):2128-36; Okayama H, Saito M, Oue N, et al. NOS2 enhances KRAS-induced lung carcinogenesis, inflammation and microRNA-21 expression. Int J Cancer 2013; 132(1):9-18; Wang Z X, Bian H B, Wang J R, et al. Prognostic significance of serum miRNA-21 expression in human non-small cell lung cancer. J Surg Oncol 2011; 104(7):847-51). Moreover, inhibition of miR-21 expression has been found to reverse such phenotypes in model systems (Yang B, Lin H, Xiao J, et al. The muscle-specific microRNA miR-1 regulates cardiac arrhythmogenic potential by targeting GJA1 and KCNJ2. Nat Med 2007; 13(4):486-91; Ren J, Zhu D, Liu M, et al. Downregulation of miR-21 modulates Ras expression to promote apoptosis and suppress invasion of Laryngeal squamous cell carcinoma. Eur J Cancer 2010; 46(18):3409-16).

Thus, in one embodiment the presence of cancer is detected by measuring the level of one or more biomarkers in conjunction with the level of one or more microRNAs. Methods of measuring miRNA levels are known to those skilled in the art. According to the present invention, the level of miRNA may or may not be determined at the same time as the level of the one or more biomarker of the present invention. Similarly, the level of miRNA may or may not be determined using the sample from which the level of the one or more biomarker is determined. In one embodiment, the cancer is lung cancer. In one embodiment, the cancer is adenocarcinoma or squamous cell carcinoma. In one embodiment, the one or more biomarker is selected from the group consisting of creatine riboside, metabolite 561+, cortisol sulfate and N-acetylneuraminic acid.

Also included in the present invention are kits useful for practicing the disclosed methods of the present invention. Thus, one embodiment of the present invention is a kit for identifying an individual having cancer, in accordance with the present invention, the kit comprising i) reagents for selectively detecting the presence, absence or level of, at least one or more biomarkers in a sample obtained from the subject and ii) instructions for using the kit. One embodiment of the present invention is a kit for detecting cancer or identifying an individual having cancer, in accordance with the present invention, the kit comprising i) reagents for selectively detecting the presence, absence or level of, at least one biomarker of the present invention in a sample obtained from the subject and ii) instructions for using the kit.

Kits of the present invention will contain at least some of the reagents required to determine the presence, absence or level of biomarkers of the present invention. Reagents for kits of the present invention can include, but are not limited to, isolated biomarkers of the present invention, and compounds that bind biomarkers of the present invention (e.g., an antibody that selectively binds to a biomarker of the present invention). In some embodiments, the biomarker protein and/or the biomarker-binding compound may be fixed to a solid substrate. The kits may further comprise control proteins. One skilled in the art will, without undue experiments, be able to select the necessary reagents from the disclosure herein, in accordance with the usual requirements. Reagents of the kit may also comprise a molecular label or tag.

Kits of the present invention can also comprise various reagents, such as buffers, necessary to practice the methods of the invention, as known in the art. These reagents or buffers may, for example, be useful to extract and/or purify biomarkers from the biological sample obtained from the subject. The kit may also comprise all the necessary material such as microcentrifuge tubes necessary to practice the methods of the invention.

EXAMPLES

Example 1

This Example demonstrates the methodology used to identify biomarkers of the present invention.

Urine samples from 469 lung cancer patients prior to treatment and 536 population controls collected from 1998 to 2007 from the greater Baltimore, Md. area were used as a training set. Patients were recruited from pathology departments in seven hospitals: Baltimore Veterans Administration Medical Center, Bon Secours Hospital, Harbor Hospital Center, Sinai Hospital, Johns Hopkins Bayview Medical Center, The Johns Hopkins Hospital, and University of Maryland Medical Center. Population controls were identified from the Department of Motor Vehicles lists and frequency-matched to cases by age, gender, and ethnicity (Zheng Y L, Loffredo C A, Yu Z, et al. Bleomycin-induced chromosome breaks as a risk marker for lung cancer: a case-control study with population and hospital controls. Carcinogenesis 2003; 24:269-74; Olivo-Marston S E, Yang P, Mechanic L E, et al. Childhood exposure to secondhand smoke and functional mannose binding lectin polymorphisms are associated with increased lung cancer risk. Cancer Epidemiol Biomarkers Prev 2009; 18:3375-83; Zheng Y L, Kosti O, Loffredo C A, et al. Elevated lung cancer risk is associated with deficiencies in cell cycle checkpoints: genotype and phenotype analyses from a case-control study. Int J Cancer 2010; 126:2199-210). An additional set of 80 recently diagnosed cases and 78 population controls were used as a validation set. Forty-eight cancerous and non-cancerous stage I tissue pairs, of which 20 are a subset of the training set, were also utilized. Survival times were calculated as time of diagnosis to time of death or to follow-up (2010); death due to cancer was determined from the NDI extraction of the death certificates. This study is approved by the Institutional Review Boards of the seven institutions. Urine biospecimens were collected prior to the administration of chemotherapy. The patient characteristics for each sample set are shown below in Table 1.

TABLE 1

| | Sample characteristics. | | | | | | |
|---|---|---|---|---|---|---|---|
| | Trainining Set | | | Validation Set [†] | | | Tissue Set |
| | All (N = 1005) | Cases (N = 469) | Population Controls (N = 536) | All (N = 158) | Cases (N = 80) | Population Controls (N = 78) | Tumor/Adjacent Normal Pairs (N = 48) |
| Age | (mean = 66.4) | (mean = 66.2) | (mean = 66.6) | (mean = 66.7) | (mean = 64.2) | (mean = 68.7) | (mean = 68.9) |
| >mean | 519 | 240 | 279 | 82 | 35 | 47 | 27 |
| <=mean | 486 | 229 | 257 | 76 | 45 | 31 | 21 |
| Smoking | | | | | | | |

TABLE 1-continued

Sample characteristics.

| | Training Set | | | Validation Set [†] | | | Tissue Set |
|---|---|---|---|---|---|---|---|
| | All (N = 1005) | Cases (N = 469) | Population Controls (N = 536) | All (N = 158) | Cases (N = 80) | Population Controls (N = 78) | Tumor/Adjacent Normal Pairs (N = 48) |
| Status | | | | | | | |
| Ever | | | | | | | 10 |
| Current | 293 | 222 | 71 | 46 | 38 | 8 | 17 |
| Former | 463 | 214 | 249 | 73 | 31 | 42 | 17 |
| Never | 249 | 33 | 216 | 39 | 11 | 28 | 4 |
| Histology | | | | | | | |
| ADC | | 216 | | | 51 | | 31 |
| SCC | | 122 | | | 14 | | 16 |
| NSCLC | | 131 | | | 10 | | 1 |
| Gender | | | | | | | |
| Female | 492 | 232 | 260 | 81 | 46 | 35 | 24 |
| Male | 513 | 237 | 276 | 77 | 34 | 43 | 24 |
| Race | | | | | | | |
| African American | 366 | 127 | 239 | 70 | 35 | 35 | 9 |
| Caucasian | 639 | 342 | 297 | 88 | 45 | 43 | 39 |
| Stage* | | | | | | | |
| I-II | | 213 | | | 31 | | 48 |
| III-IV | | 103 | | | 41 | | 0 |

*Only pathologically staged cases, according to the 7th edition of the Cancer Staging Manual of the American Joint Committee on Cancer, were utilized for stratified analyses.
[†] Five samples are missing histology, and eight samples are missing stage information.

Detailed clinical information derived from extensive questionnaires was available for each patient, including age, gender, race, smoking status (never smokers, having smoked less than 100 cigarettes in their lifetime; former smokers, having quit smoking at least 6 months prior to the interview date), pack years, histology, AJCC staging, and survival. Lung cancer diagnosis was pathologically determined. Staging was performed by a pathologist using the seventh edition of the Cancer Staging Manual of the American Joint Committee on Cancer (AJCC) (Edge S, Byrd D R, Compton C C, Fritz A G, Greene F L, Trotti A, ed. AJCC Cancer Staging Manual. 7th ed: Springer-Verlag; 2010).

Urine samples were analyzed using a quadrupole time-of-flight (QTOF) mass spectrometer (Premier, Waters), in positive (ESI+) and negative (ESI−) electrospray ionization modes, using a 50×2.1 mm Acquity 1.7 μm C18 column (Waters Corp, Millford, Mass.). Briefly, urine samples were diluted with an equal volume of 50% aqueous acetonitrile containing debrisoquine (ESI+ internal standard) and 4-nitrobenzoic acid (ESI− internal standard). Samples were centrifuged at 14,000×g for 20 minutes at 4° C. to precipitate proteins. Five μl was chromatographed on a 50×2.1 mm Acquity BEH 1.7 μm C18 column (Waters) using an Acquity UPLC system (Waters). To avoid artifacts based on sample injection order, the order was randomized. The gradient mobile phase consisted of 0.1% formic acid (A) and acetonitrile containing 0.1% formic acid (B). A typical 10-min sample run (at 0.5 ml/min) consisted of 0.5 min of 100% solvent A followed by a linear gradient to 80% A at 4 min, to 5% A at 8 min. After a 0.5 min wash step, the column was equilibrated to initial conditions for 1.5 min. The eluent was introduced by electrospray ionization into the QTOF mass spectrometer (Premier, Waters) operating in positive (ESI+) or negative (ESI−) ionization mode. The capillary and sampling cone voltages were set to 3,000 and 30 V, respectively. Source and desolvation temperatures were set to 120° C. and 350° C., respectively, and the cone and desolvation gas flows were set to 50.0 and 650.0 L/h, respectively. To maintain mass accuracy, sulfadimethoxine at a concentration of 300 pg/μl in 50% aqueous acetonitrile was used as a lock mass and injected at a rate of 50 μl/min. For MS scanning, data were acquired in centroid mode from 50 to 850 m/z and for tandem MS the collision energy was ramped from 5 to 35 V. Four different quality control sets were included with the runs to assess machine sensitivity and sample carry over. First, 169 "pooled" samples, containing aliquots from 108 urine samples, were processed randomly throughout the run. Second, a standard cocktail containing theophylline, caffeine, hippuric acid, 4-nitrobenzoic acid, and nortriptyline (designated as MetMix) was injected every 100 samples. Third, 32 blanks were randomly injected to assess sample carry over. Fourth, 48 samples with 4 high purity nicotine metabolite standards, including cotinine, nicotine-N'-oxide, anabasine, and trans-3'-hydroxycotinine (Sigma-Aldrich), were spiked into urine. Fifth, 10% of the samples were randomly selected and processed in duplicate at the end of the run to evaluate chromatogram consistency. Finally, debrisoquine and 4-nitrobenzoic acid were spiked into samples for runs in ESI+ and ESI− modes, respectively.

Chromatograms from the training set (N=1005) were visually inspected using Mass Lynx (Waters), and peaks were extracted, retention times aligned, and peak areas quantitated using the freely available R package XCMS[48]. ESI+ and ESI− peak areas were normalized using the MSTUS method (Warrack B, Hnatyshyn S, Ott K H, Zhang H, Sanders M. Proceedings of the 54th ASMS Conference on Mass Spectrometry and Allied Topics. In: Conference on Mass Spectrometry and Allied Topics 2006; Seattle, Wash.; 2006). Chromatograms from the quantitation (N=198), validation (N=158) and the tissue sets (N=48) were processed using MarkerLynx (peak areas of the training and validation sets were normalized to total ion count [TIC]). In the training set, chromatograms were first visually inspected using MassLynx (Waters Corp., Milford, Mass.) to ensure their quality and 12 samples were removed due to poor quality (e.g. undetectable spiked in control, break in signal). All subsequent data analyses were performed using R, a freely available language and environment for statistical computing and graphics (Breiman L. Random Forests. Machine Learning 2001; 45:5-32; Ho T K. Random Decision Forest. Proceedings of the 3rd International Conference). The R package XCMS (Smith C A, Want E J, O'Maille G, et al. XCMS: processing mass spectrometry data for metabolite profiling using nonlinear peak alignment, matching, and identification. Anal Chem 2006; 78(3):779-87.), version 1.22.1, was utilized to extract and align peaks for all detected metabolites. Peak areas for all signals were extracted using the following criteria: ppm=25, mzdiff=-0.005, snthresh=10, scanrange=c(1,500), peakwidth=c(5, 12), prefilter=c(1,30)). Retention times were aligned with one iteration of the rector( ) function using the loess method, which performs smoothing of the retention time deviations for every time point in each sample. Peaks were then found using the group( ) function with the following parameters: bw=10, minfrac=0.1, mzwid=0.01. Next, ESI+ and ESI- signals were merged in lung cancer cases and healthy control samples that were in common between both sets (N=1257) and signals with masses that had a ppm error larger than 50 were removed from further analysis. This filtering reduced the total number of signals from 2756 and 1804 to 1807 and 1359, for ESI+ and ESI- modes, respectively. Next, a normalization algorithm analogous to MSTUS (MS 'total useful signal') (Warrack B, Hnatyshyn S, Ott K H, Zhang H, Sanders M. Proceedings of the 54th ASMS Conference on Mass Spectrometry and Allied Topics. In: *Conference on Mass Spectrometry and Allied Topics Seattle*, Wash., 2006) was applied. Signals that are putative xenobiotics (e.g., acetaminophen) were removed before calculating the scaling factor using the following criteria: signals with very high abundance (>90th percentile) in at most 100 samples and with very low abundance (<=20th percentile) in at least 800 samples. Scaling factors, total intensity counts for each sample divided by the mean total intensity counts of all samples, were then used to normalize signal abundances. Finally, signals with variation (measured by coefficients of variation) between duplicates higher than variations between randomly selected sample pairs were removed.

The validation set data from 158 samples was also processed using XCMS R package following the same parameters outlined for the original set.

The quantitation (N=198) and the tissue sets (N=96) were processed using TargetLynx software (Waters), by extracting only the four ions of interest and using the following parameters: chromatogram mass window of 20 ppm; retention time windows of 0.35 min (creatine riboside), 0.15 (561+), 0.2 (cortisol sulfate), 0.1 (N-acetylneuraminic acid); smoothing enabled; smoothing method (1); smoothing iterations (1); smoothing width (1); apex track enabled; peak to peak baseline noise automatically calculated; peak width @ 5% height (0.130); baseline start and end (0.00, 0.50); detection of shoulder peaks disabled; threshold parameters: relative and absolute height disabled, threshold relative area (10), threshold absolute area disabled; integration window extent (1); propagation of integration parameters disabled.

Identification of putative biomarkers was initiated by searching their high accuracy masses in METLIN and HMDB databases (Wishart D S, Tzur D, Knox C, et al. HMDB: the Human Metabolome Database. Nucleic Acids Res 2007; 35:D521-6; Smith C A, O'Maille G, Want E J, et al. METLIN: a metabolite mass spectral database. Ther Drug Monit 2005; 27:747-51). If no database hits were returned, spectral interpretation of the MS/MS product ion mass and MS3 spectra were used to generate putative structures. Metabolite identity was confirmed using commercially available and in-house synthesized standards, by comparison of retention time, product ion mass spectra and by monitoring characteristic fragmentation patterns in multiple reaction monitoring (MRM) mode. The structure of the novel metabolite, creatine riboside, was also confirmed by NMR. See FIG. 5 for m/z (mass to charge ratio), retention time and MRM specifics regarding the four molecules/biomarkers described in this invention.

Figure 3:
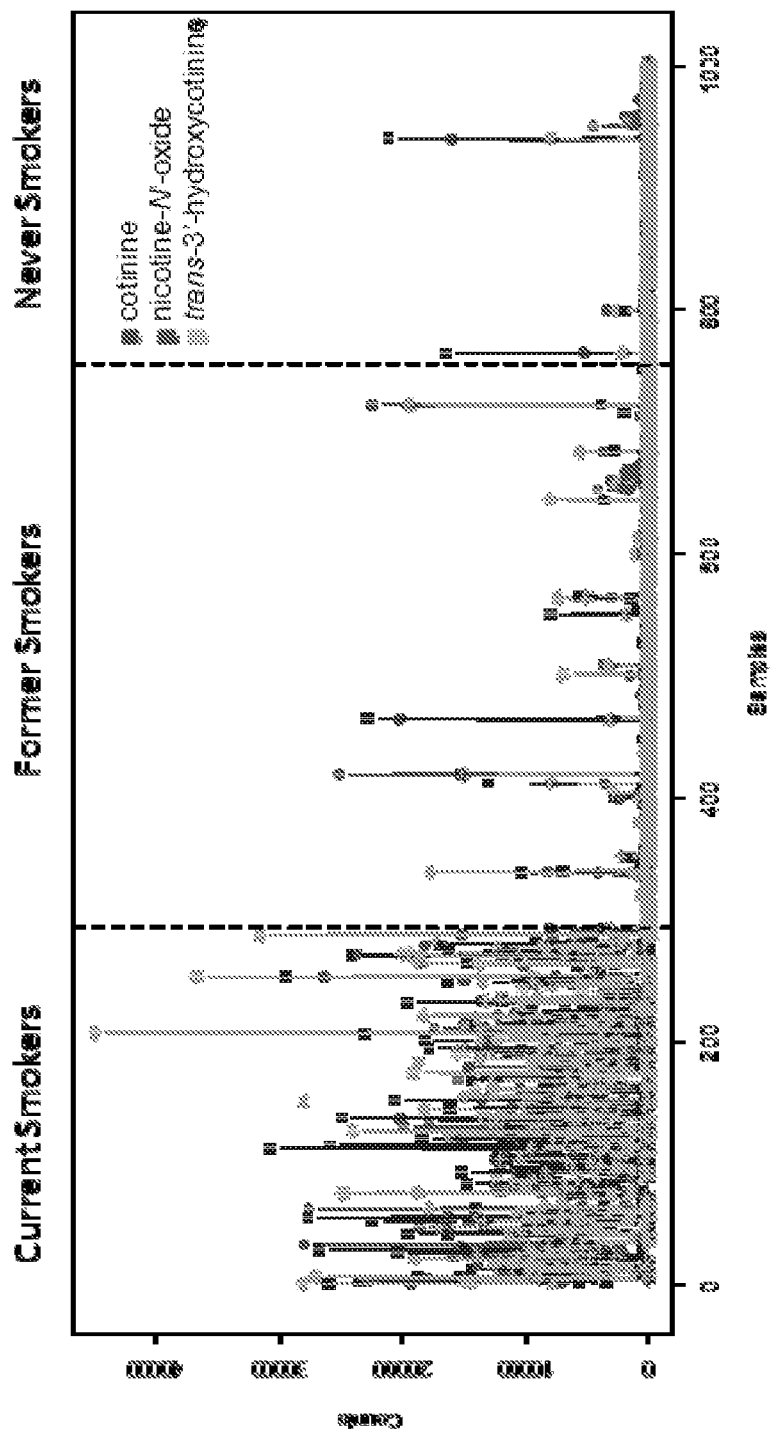
FIG. 3. Abundances of three nicotine metabolites (cotinine, nicotine-N'-oxide, and trans-3'-hydroxycotinine), stratified by smoking status, indicating correlation between the self-reported smoking status and nicotine metabolites presence and abundance in the urine.

Unsupervised clustering revealed a clear separation between urine and quality control samples, a global indication of successful measurements (FIG. 2A). To further check measurement reproducibility within a run, 169 (~15%) duplicate samples were processed randomly and showed a very strong correlation, with Spearman's r>0.85 for most samples (FIG. 2B). Furthermore, the distribution of coefficients of variation (CVs) is expectedly smaller (P<0.00001) for the quality control compared to the study subject samples (FIG. 2C). Finally, a global increase in cotinine, nicotine-N'-oxide, and trans-3'-hydroxycotinine was observed in current compared to former and non-smokers, thereby confirming the ability to detect these key metabolites (FIG. 3).

The identities of the molecules described in this invention were confirmed as follows:

The identity of N-acetylneuraminic acid (formula=C11H19NO9) was confirmed using a commercially available standard (Sigma-Aldrich, CAS#131-48-6).

The identity of cortisol sulfate (formula=C21H30O8S) was confirmed by synthesizing cortisol-21-sulfate (CAS#1253-43-6) in house. All chemicals were purchased from Sigma-Aldrich. Cortisol-21-sulfate was prepared from cortisol using modification of reported method for sulfation using chlorosulfonic acid [Lloyd A G. Fractionation of the products of the direct sulphation of monosaccharides on anion-exchange resin. Biochem J 1962; 83:455-60.]. Briefly, 0.5 gm cortisol was added to 2.5 ml dry pyridine in a round bottom flask, chilled on ice and 0.2 ml chlorosulfonic acid was added dropwise with swirling. The reaction mixture was swirled for 45 min on ice followed by the addition of 1 ml distilled water. Solvent was removed on rotary evaporator, residue re-dissolved in 20 ml water, neutralized by addition of NaHCO3. Cortisol-21-sulfatewas purified from the reaction mixture using anion exchange resin as described earlier [ref Mumma R O, Hoiberg C P, Weber W W, 2nd. Preparation of sulfate esters. The synthesis of steroid sulfates by a dicyclohexylcarbodiimide-mediated sulfation. Steroids 1969; 14(1):67-74.]. Purity of the compound was found to be >95% by NMR.

Creatine riboside (formula=C9H17N3O6) is a novel compound described herein, and synthesized in house. Synthesis of creatine riboside is based on the Maillard reaction (Hodge J E. Dehydrated foods: chemistry of browning reactions in model systems. J Agr Food Chem 1953; 1:928-43) and the knowledge that ribose is considerably more reactive than glucose [ref. Bunn H F, Higgins P J. Reaction of monosaccharides with proteins: possible evolutionary significance. Science 1981; 213(4504):222-4). In a test tube, 20 mg ammonium bicarbonate, 60 mg D-(-)-ribose, and 6 mg creatine monohydrate were combined, mixed by vortexing, and heated at 80° C. for 10 min in a shaking heating block. The synthesis product was stored at -20° C. until analysis.

Figures 1, 5:
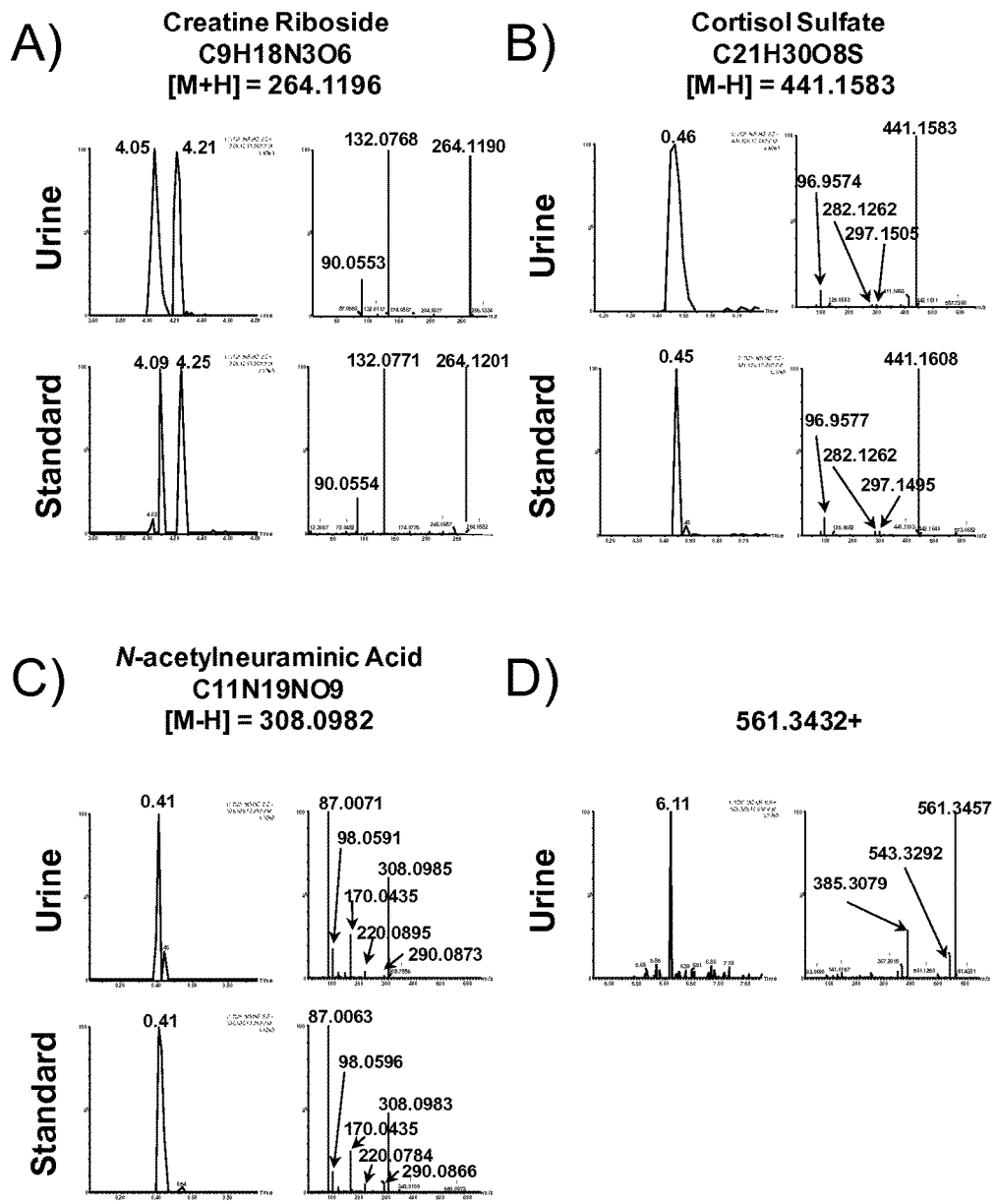
FIG. 5. MS-MS validation in comparison to commercially available and synthesized standards of A) Creatine riboside, B) Cortisol sulfate, and C) N-acetyl neuraminic acid. D) MS-MS of un-indentified metabolite 561.3432+. E) Fragmentation pattern depiction of the novel and in-house synthesized compound creatine riboside.
Figures 2, 5:
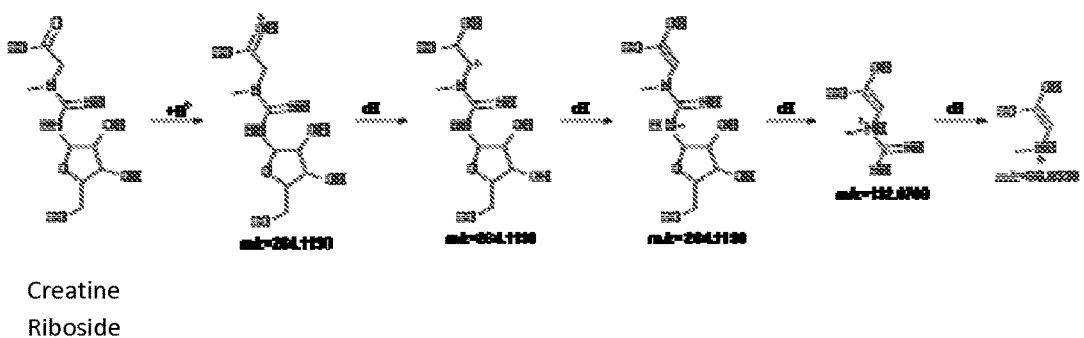

The structure of creatine riboside was determined using UPLC-QTOF MS/MS. The reaction product was separated on a Acquity BEH Amide 1.7 μm 2.1×50 mm column (Waters) which was maintained at 40° C. throughout the run under HILIC conditions using a mixture of (A) 10 mM ammonium acetate in 90% acetonitrile (pH=8.9) and (B) 10 mM ammonium acetate in 10% acetonitrile (pH=8.9) as mobile phase. The gradient elution was performed over 10 min using: 1-60% B in 4 min (0.4 ml/min), 60-80% B at 8 min (0.4 ml/min), holding at 80% B up to 8.5 min (0.3 ml/min), bringing back to 1% B at 8.8 min and holding at 1% until end (0.3 ml/min). The column was re-equilibrated with 99% A at the end of each run prior to injection of next sample. The eluent was introduced via electrospray into a Synapt G2S mass spectrometer (Waters) and tandem MS was generated for 264.1196+ corresponding to the predicted m/z for creatine riboside. Retention time and m/z were compared for the synthesized creatine riboside and the metabolite putatively identified as creatine riboside in the urine samples (FIG. 5). Further spectral interpretation was conducted using Mass Frontier v7.0 (Thermo Fisher Scientific, Waltham, Mass.) selecting the daughter ion m/z=90.0550+ as the final fragment. Results are shown in FIG. 5A, which demonstrates that the in silico predicted fragments (using the default settings) correspond with the fragments of 264.1196+ identified in the synthetic standard and urine sample.

The synthesis of creatine riboside is further supported from the $^1$H-$^{13}$C HMBC spectrum of the reaction mixture between ribose and creatine in dmso-d$^6$. HMBC is a 2D NMR experiment which gives the long range (2- or 3-bonds) couplings between protons and carbons. As can be seen (FIG. 6), there is a cross peak between the anomeric sugar proton of ribose at 4.61 ppm and the carbon at 156.19 ppm of creatine, indicating the covalent attachment between the two units.

Analysis of compound 561+ indicates the molecule is a glucoronidated lipid. The MS/MS spectra for compound 561+ from urine (FIG. 5D) shows a loss of 176, characteristic for glucuronides. This observation along with a fact that acid hydrolysis causes a complete loss of 561+ peak in urine provide evidence that 561+ is a glucoronide. Additionally, there is a loss of two 18 amu (H2O) as evident in the MSMS product ion spectrum, which would indicate two other —OH groups in addition to the one attached to glucuronic acid.

Example 2

This Example demonstrates the ability of methodology of the present invention to predict the smoking status and/or the cancer status of test individuals.

Subjects were classified by their smoking status (smokers versus nonsmokers) and 87% of the samples were correctly classified. The results of this classification are shown below in Table 2.

TABLE 2

Classification of smoking status using Random forest analysis.

| | All Signals* | | Top Predictive Signals** | |
|---|---|---|---|---|
| | % ACC(sd)*** | | % ACC(sd)*** | |
| | TPR/FPR**** | | TPR/FPR**** | # Signals |
| All Samples (469 cases and 536 controls) | 86.7(0.1) 65.5/3.9 | | 87.4(0.1) 68.5/4.3 | 350 |

*Total number of signals used: 31.55
**Top predictive signals: determined by maximizing % accuracies of 3 iterations of random forests
***% ACC (sd) average % out of bag accuracy and its standard deviation using 3 iterations
****TPR: true positive rate; FPR: false positive rate Importantly, the 3 most highly associated metabolites, ranked according to the importance score given by Random Forests, are cotinine, nicotine-N'-oxide, and trans-3'-hydroxycotinine, known nicotine metabolites. This finding establishes the utility of random forests-based classification approach to find diagnostic metabolites of lung cancer. Samples were classified as lung cancer or healthy controls using the R package randomForest (Breiman L. Random Forests. Machine Learning 2001; 45:5-32; Ho T K. Random Decision Forest. Proceedings of the 3rd International Conference). Since there are known smoking habit differences between different genders and race (Kabat G C, Morabia A, Wynder E L. Comparison of smoking habits of blacks and whites in a case-control study. Am J Public Health 1991; 81:1483-6; Okuyemi K S, Ebersole-Robinson M, Nazir N, Ahluwalia J S. African-American menthol and nonmenthol smokers: differences in smoking and cessation experiences. J Natl Med Assoc 2004; 96:1208-11), including the preference for menthol cigarettes amongst African Americans Health 1991; 81:1483-6; Okuyemi K S, Ebersole-Robinson M, Nazir N, Ahluwalia J S. African-American menthol and nonmenthol smokers: differences in smoking and cessation experiences. J Natl Med Assoc 2004; 96:1208-11; Stahre M, Okuyemi K S, Joseph A M, Fu S S. Racial/ethnic differences in menthol cigarette smoking, population quit ratios and utilization of evidence-based tobacco cessation treatments. Addiction 2010; 105 Suppl 1:75-83; Jones M R, Apelberg B J, Tellez-Plaza M, Samet J M, Navas-Acien A. Menthol Cigarettes, Race/Ethnicity and Biomarkers of Tobacco Use in US Adults: The 1999-2010 National Health and Nutrition Examination Survey (NHANES). Cancer Epidemiol Biomarkers Prev 2012), classifications of cases and controls were initially performed on all samples, then on samples stratified by race and gender. Proportion of samples that were accurately categorized as lung cancer cases or controls using optimal variables were as follows: 78.1% using all samples, 77.7% for Caucasian males, 78.6% for Caucasian females, 84.9% for African American males, and 82.3% for African American females. AS shown in Table 3 below, true positive and true negative rates ranged from 77.1-84.9 and 63.2-81.7, respectively.

Caucasian females, 84.9% for African American males, and 82.3% for African American females. As shown in Table 3 below, true positive and true negative rates ranged from 77.1-84.9 and 63.2-81.7, respectively.

TABLE 3

Classification of lung cancer status using Random forest analysis.

| | All signals | | Top Predictive Signals* | | Bottom Predictive Signals** | |
|---|---|---|---|---|---|---|
| | % ACC (sd) TPR/FPR | # Input Signals | % ACC (sd) TPR/FPR | # Input Signals | % ACC (sd) TPR/FPR | # Input Signals |
| All Samples | 72.7 (0.5) | 3166 | 78.1 (0.5) | 97 | 68.8 (0.9) | 3069 |
| (469 cases and 536 controls) | 69.1/21.2 | | 76.5/18.4 | | 64.3/24.3 | |
| Stage I Samples | 73.2 (0.9) | 3166 | 78.4 (0.7) | 87 | 71.7 (1) | 3079 |
| (204 cases and 536 controls) | 45.3/14.1 | | 63.2/14.4 | | 37.4/13.9 | |
| Caucasian Males | 71.7 (2.1) | 3166 | 77.7 (0.6) | 72 | 66 (1.3) | 3094 |
| (170 cases, 156 controls) | 73.2/26.9 | | 80.2/23.3 | | 66.3/32.6 | |
| Caucasian Females | 67.7 (1.1) | 3166 | 78.6 (0.7) | 72 | 61.5 (1.1) | 3094 |
| (172 cases, 141 controls) | 72.9/35.8 | | 81.7/22.3 | | 67.2/42.2 | |
| African American Males | 73.8 (1.5) | 3166 | 84.9 (1.2) | 102 | 70.1 (1.5) | 3064 |
| (67 cases, 120 controls) | 56/14.6 | | 80.8/9.5 | | 50.9/16.3 | |
| African American Females | 72.8 (2.1) | 3166 | 82.3 (1.1) | 152 | 67.9 (1.5) | 3014 |
| (60 cases, 119 controls) | 49.8/12.3 | | 70/10.7 | | 36.2/14.7 | |

Figure 6:
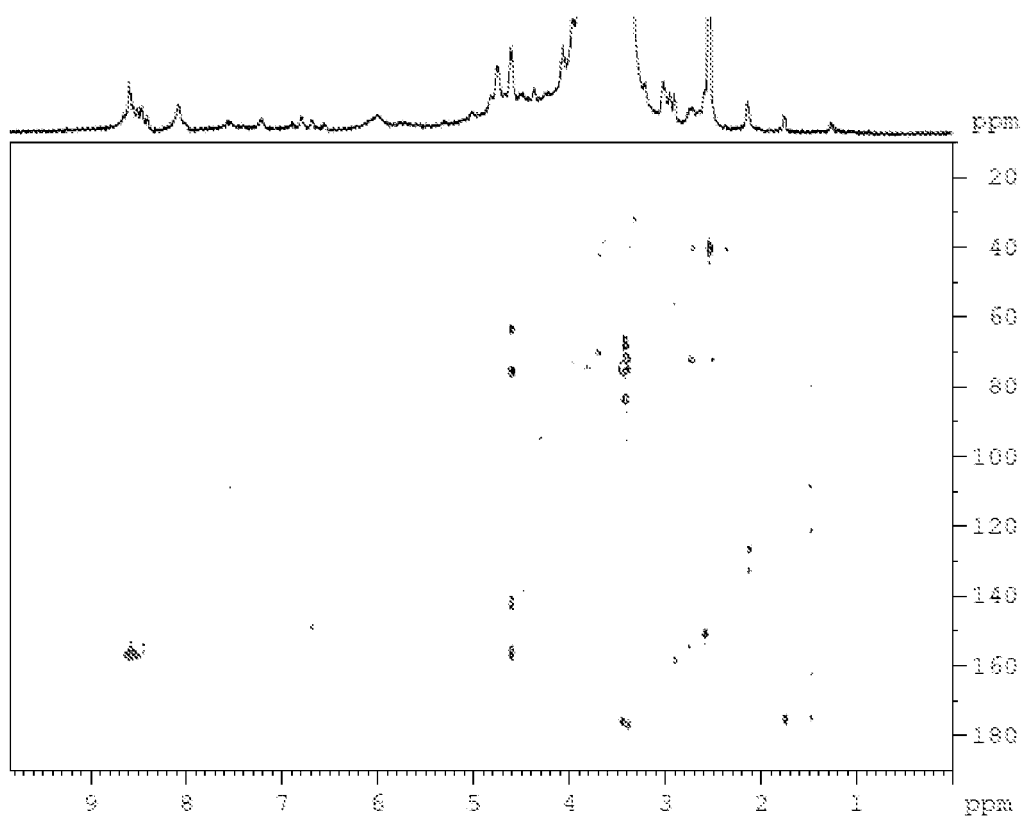
FIG. 6. NMR confirmation of creatine riboside structure. $^1H$-$^{13}C$ HMBC spectrum of the reaction mixture between ribose and creatine in dmso-$d^6$.
Figure 14:
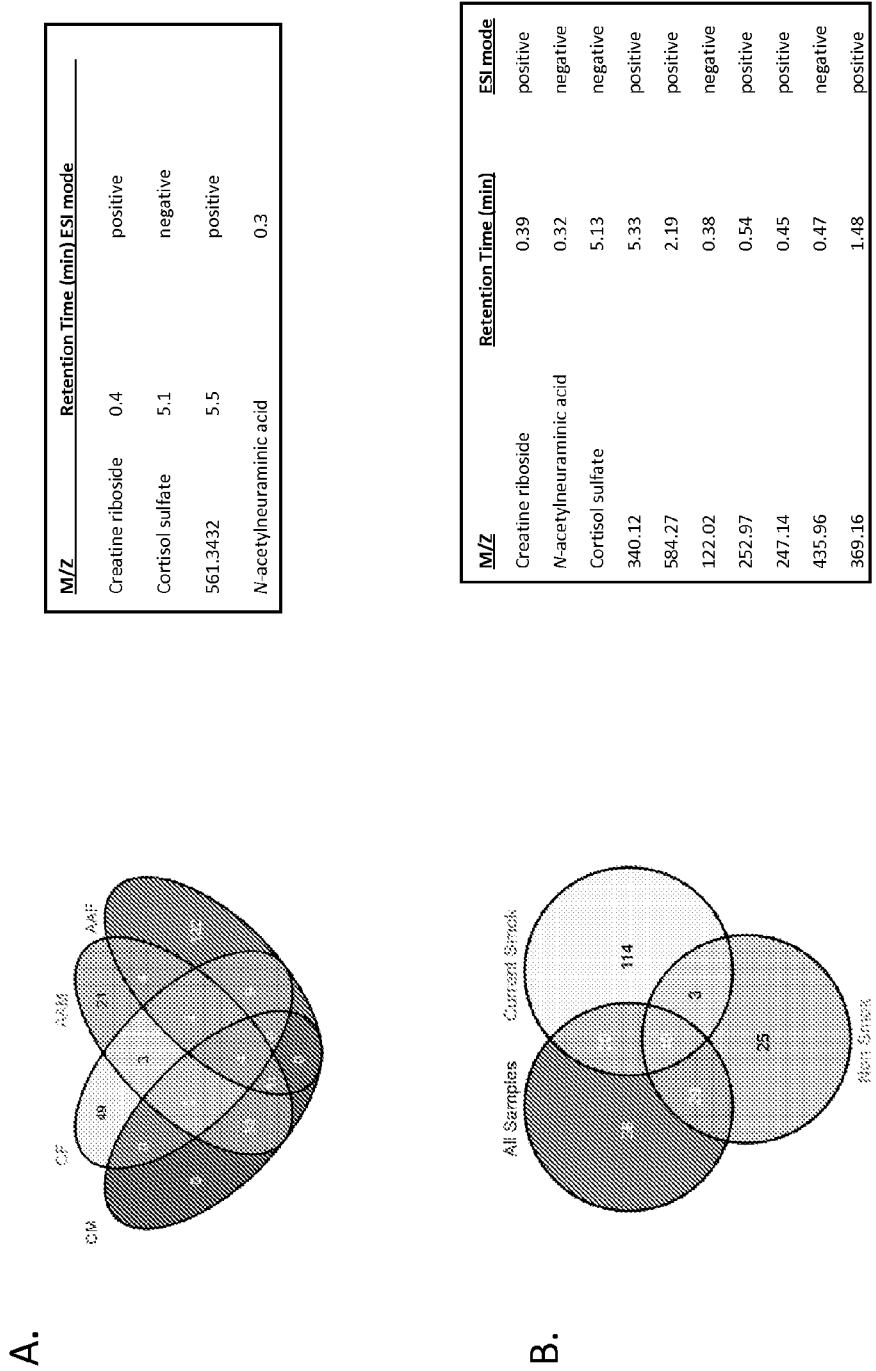
FIG. 14. Overlap between signals that are predictive of lung cancer status (using random forests) in the training set, in samples stratified by race and gender A), and smoking status B).

*Top predictive signals: determined by maximizing % accuracies of 3 iterations of random forests
** Bottom predictive signals: signals not contributing to the maximum % accuracies based on 3 iterations of random forests
% ACC (sd): average % out of bag accuracy and its standard deviation using 3 iterations
TPR: true positive rate; FPR: false positive rate Four metabolites contributed strongly to the classifications independent of race, gender and smoking status (See FIG. 14), and were elevated in the urine of lung cancer patients (P<0.00001, FIG. 4A): N-acetylneuraminic acid, cortisol sulfate, creatine riboside and one unidentified metabolite with a mass/charge ratio (m/z) of 561.3432+, confirmed to be a glucuronidated lipid compound (FIG. 5D). Creatine riboside structure was confirmed by NMR, definitively proving its novelty (FIG. 6).

Figure 4:
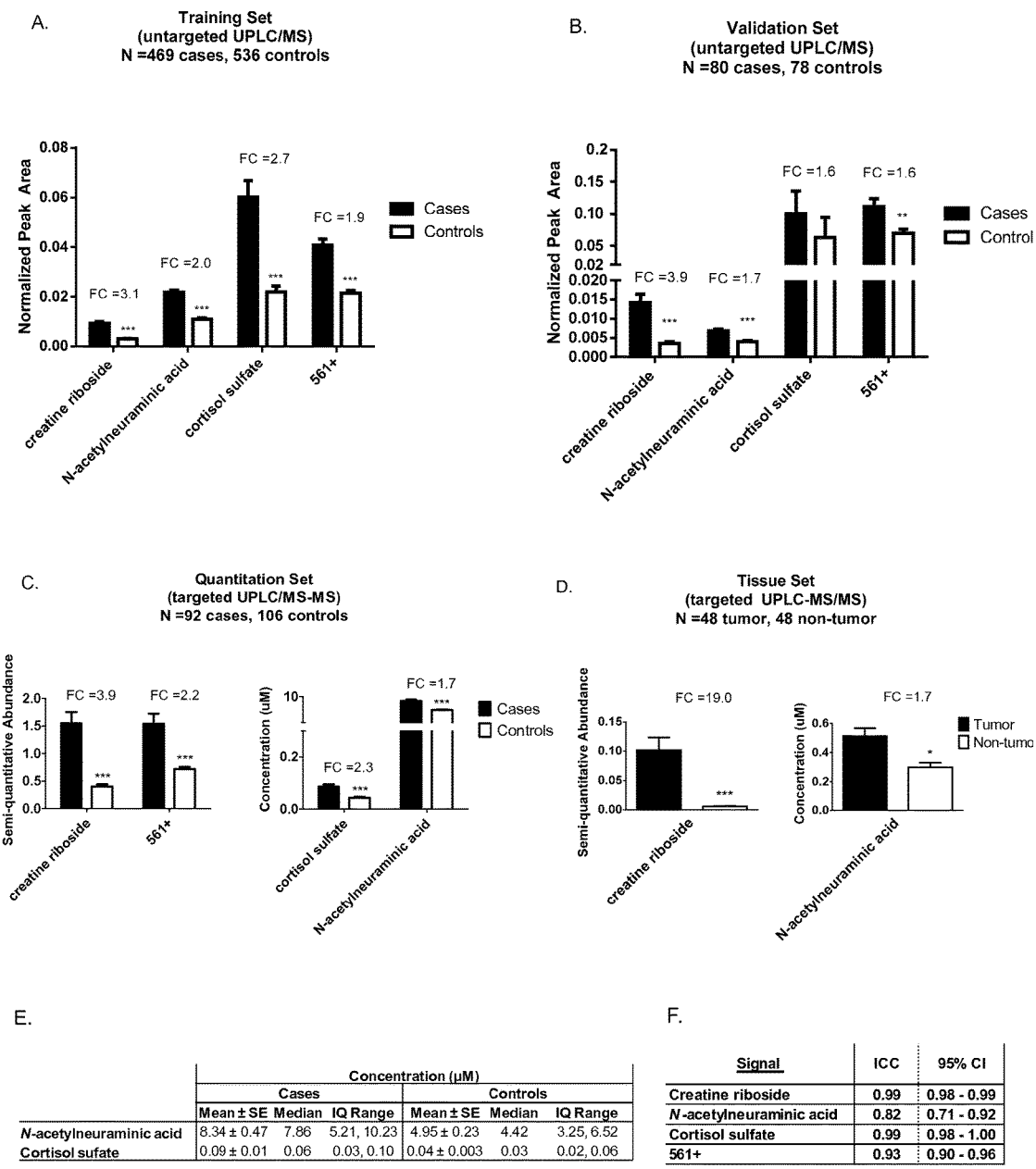
FIG. 4. Differences in abundance and validation of signals that were top contributors in the classification of patients as lung cancer or healthy controls groups. Untargeted and MSTUS normalized UPLC-MS abundances (mean and standard of the mean (SEM)) are depicted for A) the training set containing 469 cases and 536 controls, B) the validation set comprising 80 cases and 78 controls. Quantitated UPLC-MS/MS abundances (mean and SEM) in C) a subset of the training set containing 92 cases and 106 controls, D) a matched tissue set containing 48 stage I tumors and 48 adjacent non-tumor samples. E) Absolute concentration ranges of identified metabolites with available pure standards for N-acetylneuraminic acid and cortisol sulfate are shown for cases and controls. F) Intraclass correlation coefficients were calculated for the quantitated subset of 198 samples, where measurements were obtained at two time points over two years apart. FC=fold change.

Three metabolites (creatine riboside, N-acetylneuraminic acid, and metabolite 561+) were confirmed to be elevated in the urine of lung cancer patients in an independent validation set (P<0.004, Table 1, FIG. 4B) from the same cohort (N=158), comprising cases that were diagnosed more recently when compared to the training sample set. Cortisol sulfate, although not significantly elevated in cases possibly due to insufficient power, shows the expected trend. In addition, the four metabolites identified herein were technically validated on a quantitative Xevo TQ mass spectrometer in a subset (N=198) of the training set, representing similar distributions of age, gender and racial composition to the training cohort (P<0.00001, Table 1, FIG. 4C, 4E). The reproducibility of metabolite measurements was confirmed by a second quantitation carried out two years later on the same samples, resulting in intraclass correlation coefficients (ICC) from 0.82 to 0.99 (FIG. 4F).

Example 3

This Example demonstrates the presence of the identified biomarkers in tumor tissue.

Tumor and matched adjacent normal tissues were pulverized by cryogenic grinding (Cryomill®, Retsch GmbH, Haan, Germany) using a 5 mm stainless steel ball. Average sample weight was 15 mg. A monophasic mixture of ice-cold chloroform:methanol:water (2:5:2, v:v:v) was used for extraction. Samples were centrifuged at 14,000×g for 15 minutes at 4° C., and reconstituted in 70% aqueous acetonitrile before they were injected onto the Xevo TQMS system. Creatine riboside and N-acetylneuraminic acid were significantly more abundant in tumor tissue compared to adjacent normal tissue, as assessed in 48 stage I adenocarcinoma and squamous cell carcinoma patients (FIG. 4D). Creatine was also elevated in the tumor compared to adjacent normal tissue, and correlates with creatine riboside (FIG. 7).

Example 4

This Example illustrates an assessment of the contribution of each metabolite to lung cancer.

Figures 2, 8:
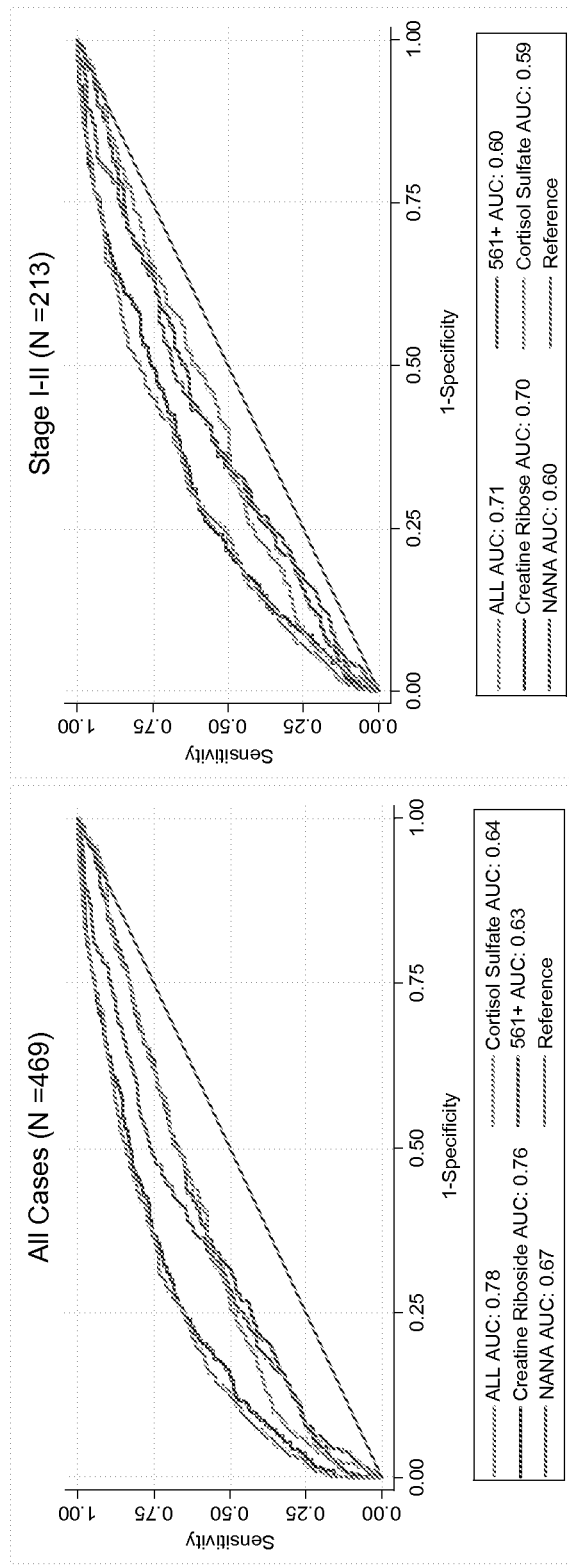
FIG. 8. Association of top four metabolites with lung cancer diagnosis. Signal abundances are dichotomized using the third quartile of healthy control abundances as a cutoff. A) Logistic regression results with reported false discovery rate (FDR) values based on Benjamini-Hochberg method. B) ROC analysis of individual metabolites and their combination in all cases, and in stage I-II cases.
Figure 9:
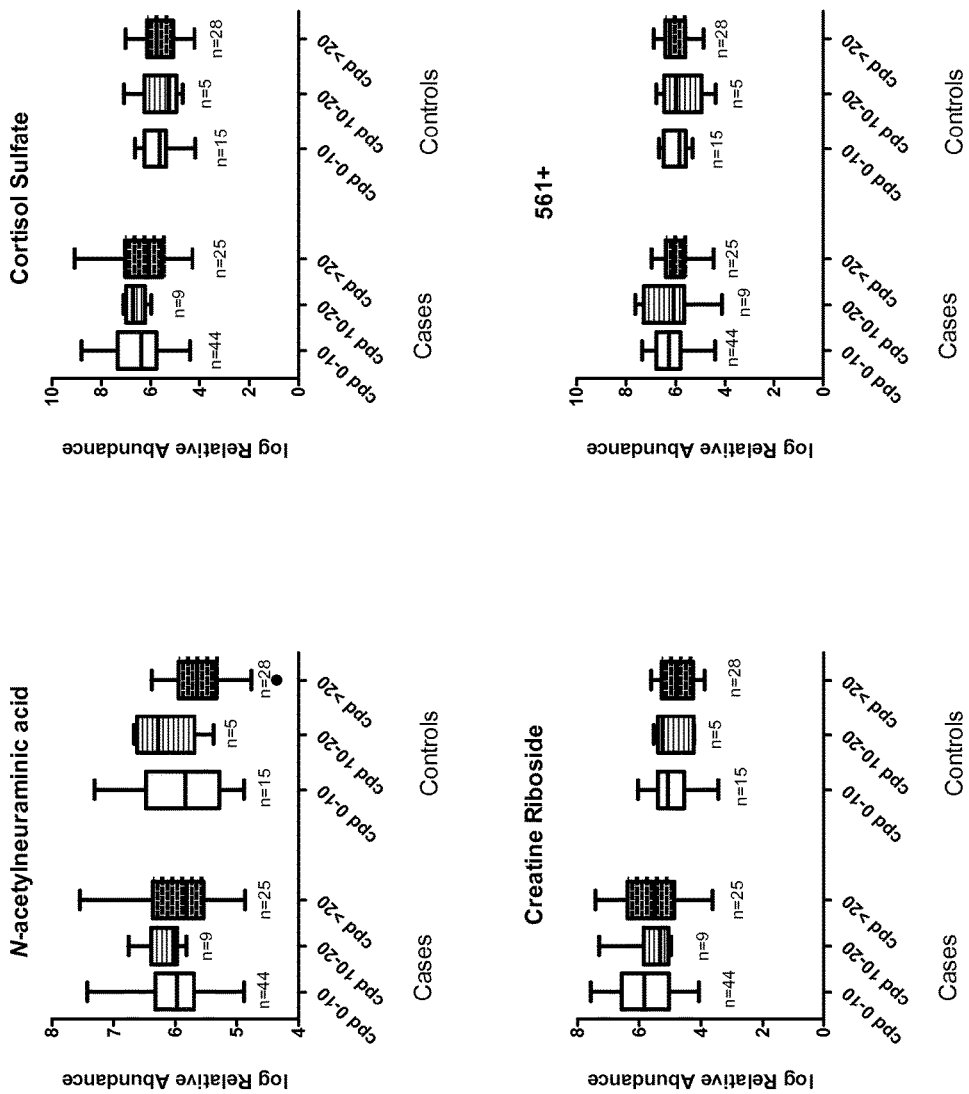
FIG. 9. Relative abundances of the top four diagnostic and prognostic biomarkers stratified by cigarettes per day (cpd) of self-reported smoking 48 hours prior to the interview in the training set (78 lung cancer cases and 48 population controls). There were no statistically significant differences of abundances observed across the strata.
Figures 1, 10:
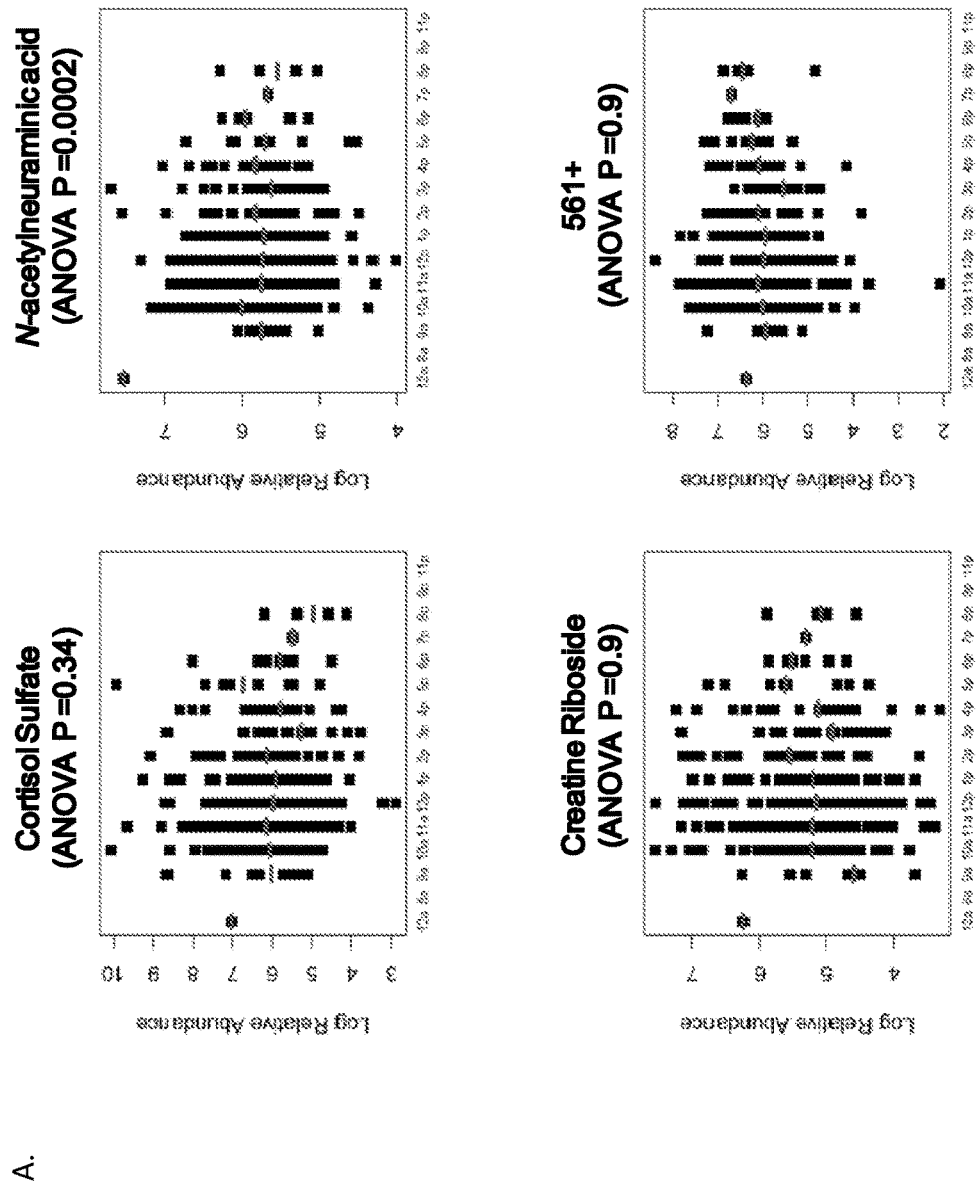
FIG. 10. Diurnal effects on urine metabolites in the training set. Distribution plots depicting relative signal abundances across urine collection times (a—am, p—pm) in A) lung cancer cases and B) population controls.
Figures 2, 10:
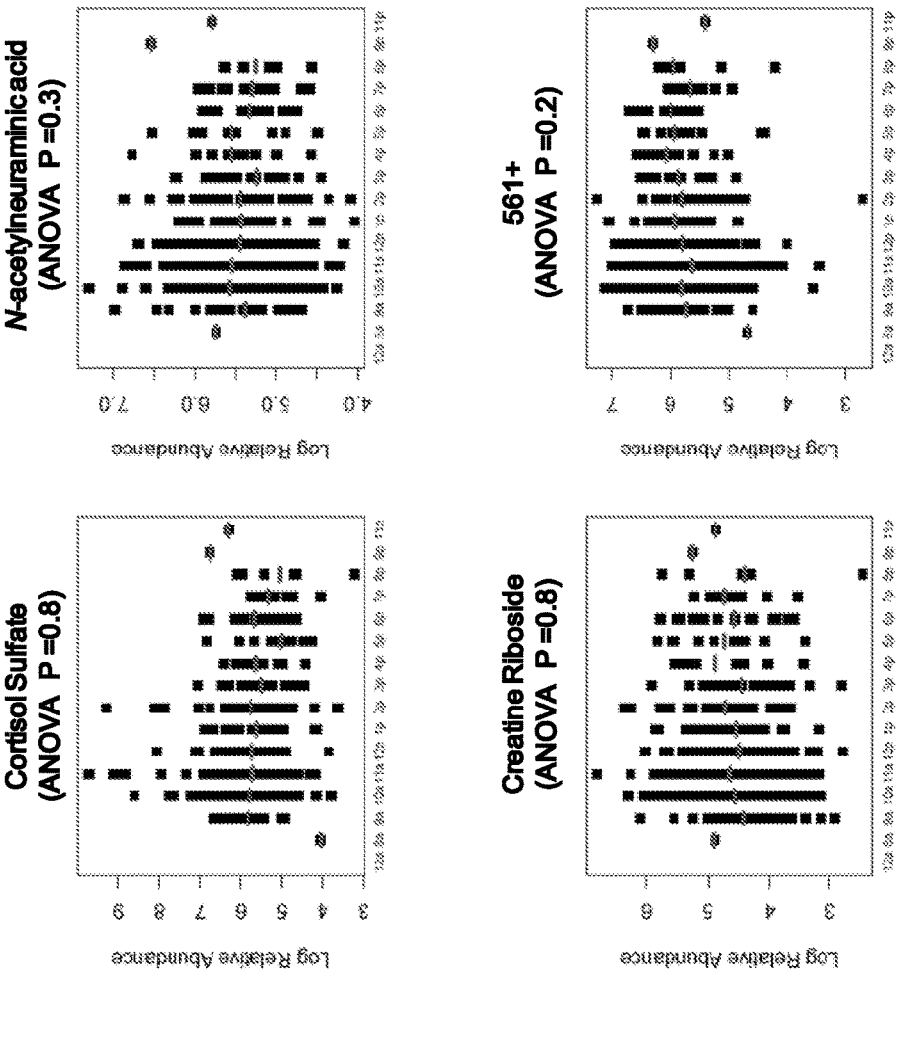

To assess the contribution of each metabolite to lung cancer risk, we performed logistic regression in all and in early stage I-II cases (FIG. 8A), adjusting for race, gender, interview year, smoking status, pack years and urine collection. Logistic regression was performed in STATA (Stata Statistical Software Release 11.2, College Station, Tex.). P-values were corrected for multiple hypotheses testing using false discovery rate method by Benjamini and Hochberg (Benjamini Y, Hochberg Y. Controlling the False Discovery Rate: A Practical and Powerful Approach to Multiple Testing. Journal of the Royal Statistical Society Series B (Methodological) 1995; 57:11.). Of note, associations are independent of histology (data not shown). Additionally, the number of cigarettes per day is not associated with the levels of the top four biomarkers in either the cases or the controls (FIG. 9). However, N-acetylneuraminic acid levels do show some diurnal variation (FIG. 10), and therefore all analyses were adjusted for the time of day urine was collected. ROC analysis resulted in areas under the curve (AUC) ranging from 0.63 to 0.76 for all cases, and 0.59 to 0.70 for early stage cases (FIG. 8B), using individual metabolites. Models using creatine riboside or all four biomarkers in all and in early stage cases are significantly more predictive (P<0.00001) than models using the other 3 metabolites individually.

Example 5

This Example illustrates an assessment of the association between levels of biomarkers of the present invention and prognosis.

Survival analyses were performed in SAS Enterprise Guide, version 4.2 (SAS Institute Inc.) and all reported P values were two-sided. Signal abundances were dichotomized into binary variables using a tertile cutoff, based on the distribution of the abundances of the healthy controls. Cox models with left truncation were performed to account for the lag time, up to two years, between diagnosis and urine collection dates. Multivariate Cox models were adjusted for urine collection time, histology, stage, race, gender, interview year, pack years and smoking status. The proportional hazards assumption was tested and if not met, the hazard ratio function was calculated separately before and after a given time point. This cutoff was determined by the time at which the survival curves started to diverge/converge and by ensuring that the β coefficients of the signal-time term before and after were no longer significant. As shown below in Table 4, after adjusting for gender, race, stage, histology, smoking status, pack years, interview year, and urine collection time, high levels of cortisol sulfate (HR=1.49 (P=0.003), creatine riboside (HR=1.76 (P=0.0003) in the first 45 months), N-acetylneuraminic acid (HR=1.57 (P=0.02) in the first 15 months) and 561+ (HR=1.97 (P<0.00001) in the first 20 months) are associated with worse survival (also see FIG. 11A for Kaplan-Meier plots).

TABLE 4

Cox proportional hazards regression results are depicted for both all cases, and stage I-II cases in the training set.

| Signal | Univariate | | | Multivariate* | | |
|---|---|---|---|---|---|---|
| | HR (95% CI) | P | FDR† | HR (95% CI) | P | FDR† |
| All Cases (N = 469) | | | | | | |
| N-acetylneuraminic acid | | | | | | |
| <=15 months | 1.74 (1.22-2.48) | 0.002 | 0.06 | 1.57 (1.07-2.29) | 0.02 | 0.20 |
| >15 months | 1.14 (0.82-1.57) | 0.44 | | 1.26 (0.90-1.78) | 0.19 | |
| Cortisol sulfate | 1.53 (1.21-1.94) | 0.0004 | 0.01 | 1.49 (1.15-1.94) | 0.003 | 0.03 |
| Creatine riboside | | | | | | |
| <=45 months | 2.05 (1.54-2.71) | <0.0001 | 0.0005 | 1.76 (1.29-2.39) | 0.0003 | 0.003 |
| >45 months | 0.86 (0.38-1.95) | 0.72 | | 0.79 (0.34-0.85) | 0.59 | |
| 561+ | | | | | | |
| <=20 months | 2.32 (1.70-3.15) | <0.0001 | 0.001 | 1.97 (1.41-2.75) | <0.0001 | 0.003 |
| >20 months | 1.05 (0.70-1.55) | 0.83 | | 0.88 (0.57-2.75) | 0.54 | |
| Stage I-II Cases (N = 213) | | | | | | |
| N-acetylneuraminic acid | 0.70 (0.41-1.19) | 0.18 | 0.89 | 0.64 (0.36-1.12) | 0.12 | 0.81 |
| Cortisol sulfate | 1.45 (0.90-2.32) | 0.12 | 0.89 | 1.43 (0.87-2.35) | 0.16 | 0.81 |
| Creatine riboside | 1.78 (1.08-2.93) | 0.02 | 0.81 | 1.83 (1.08-3.09) | 0.03 | 0.64 |
| 561+ | | | | | | |
| <=15 months | 7.83 (2.23-27.51) | 0.001 | 0.60 | 9.33 (2.62-33.23) | 0.0006 | 0.20 |
| >15 months | 0.83 (0.45-1.52) | 0.54 | | 1.02 (0.54-1.95) | 0.95 | |

Figures 1, 11:
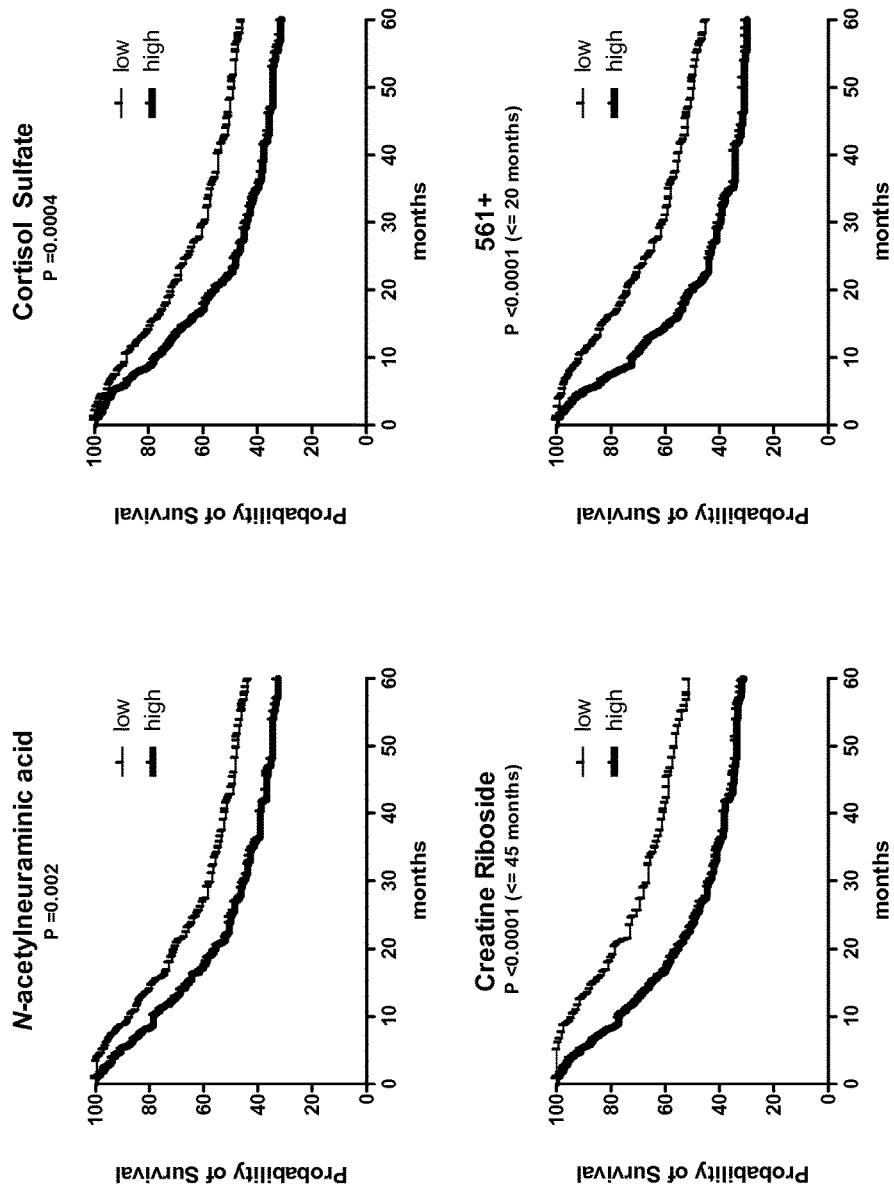
FIG. 11. Kaplan-Meier survival estimates are depicted for top four biomarkers. Metabolites significantly associated with prognosis in A) all lung cancer patients and B) stage I-II lung cancer patients are shown. The P values reported in the Kaplan-Meier plots reflect the maximum likelihood estimates generated using a univariate Cox model, taking into account left truncation (the lag time between diagnosis and time of urine collection). C) Combination of putative diagnostic and prognostic biomarkers is shown for all cases, and stage I-II cases. Only metabolites that showed statistically significant associations with survival, independent of clinical factors, were combined. As such, scores derived for cortisol sulfate, N-acetylneuraminic acid, creatine riboside and 561+ were combined for the analysis of all cases; creatine riboside and 561+ scores were combined for the analysis of stage I-II cases.
Figures 2, 11:
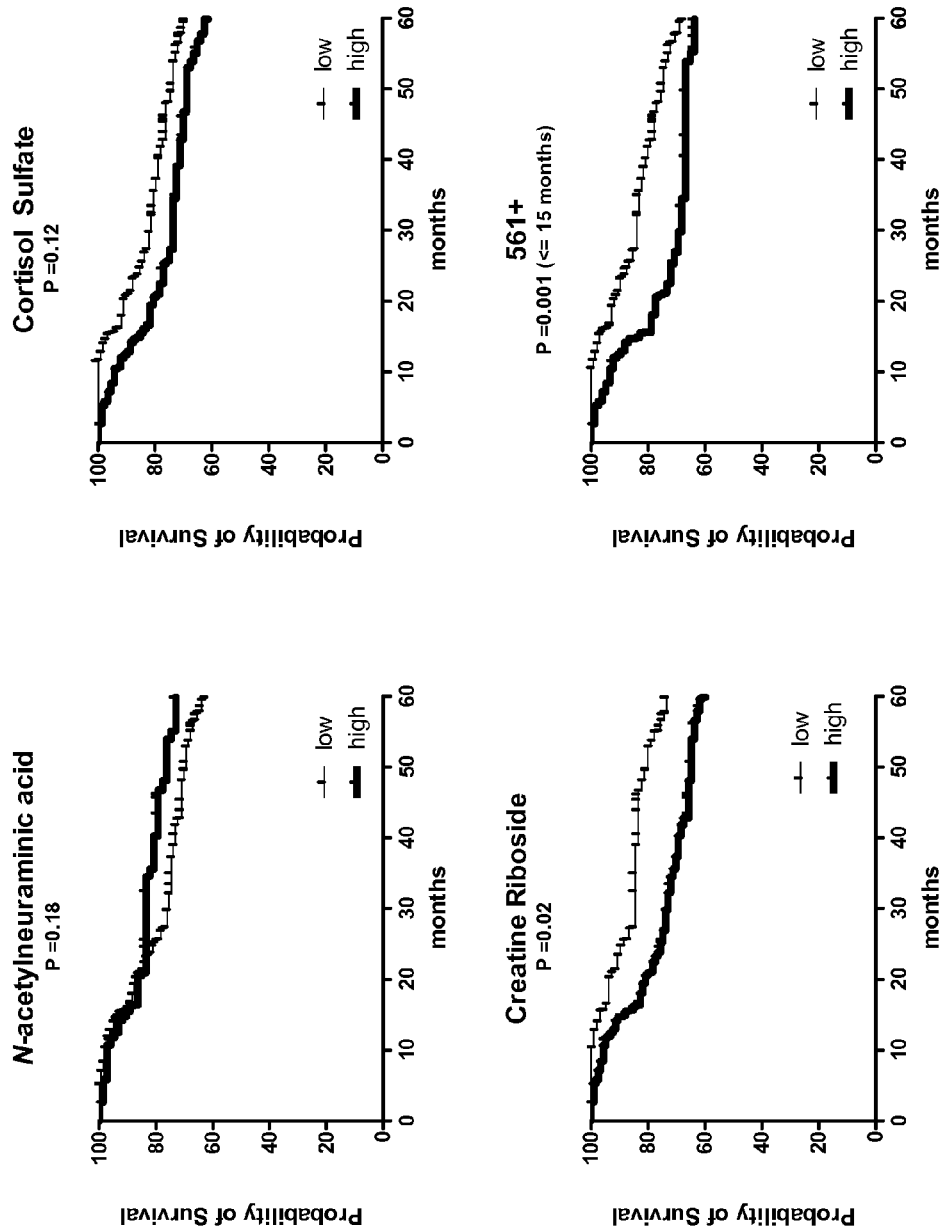
Figures 3, 11:
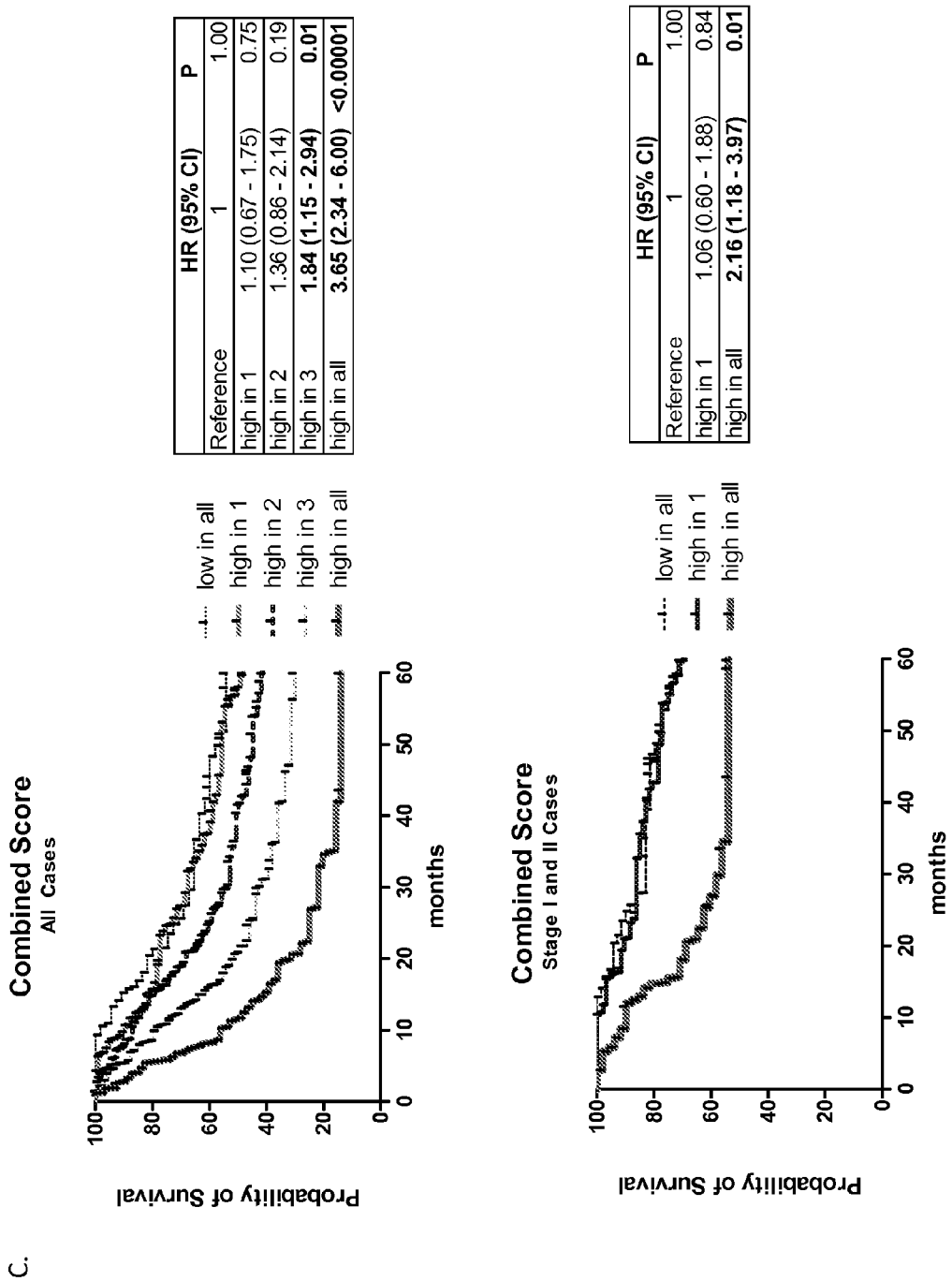
Figures 1, 12:
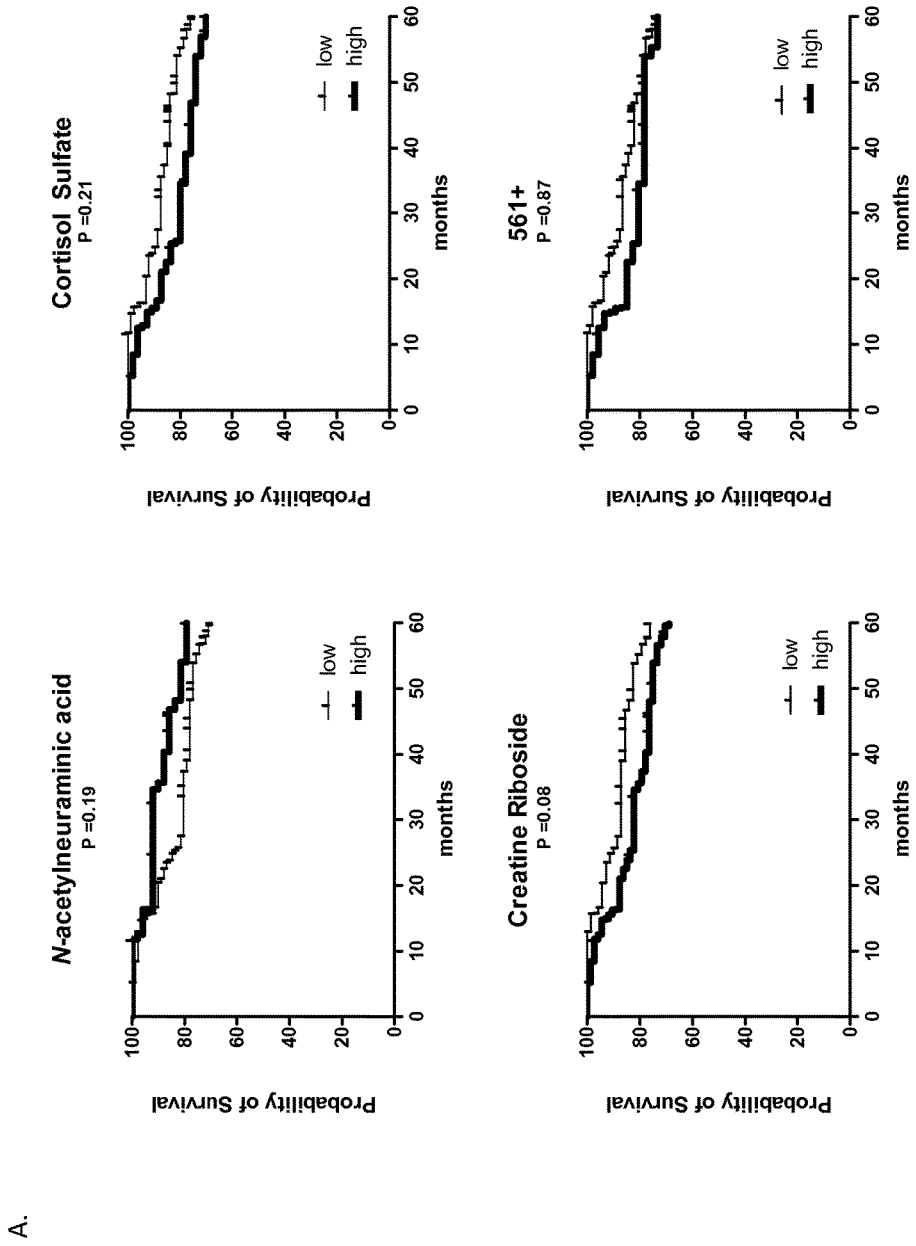
FIG. 12. Survival analysis stratified by stage in training set samples (N=469). Kaplan-Meier survival plots A) and Cox proportional hazards regression analysis, taking in to account left truncation of the top four diagnostic and prognostic biomarkers B).
Figures 2, 12:
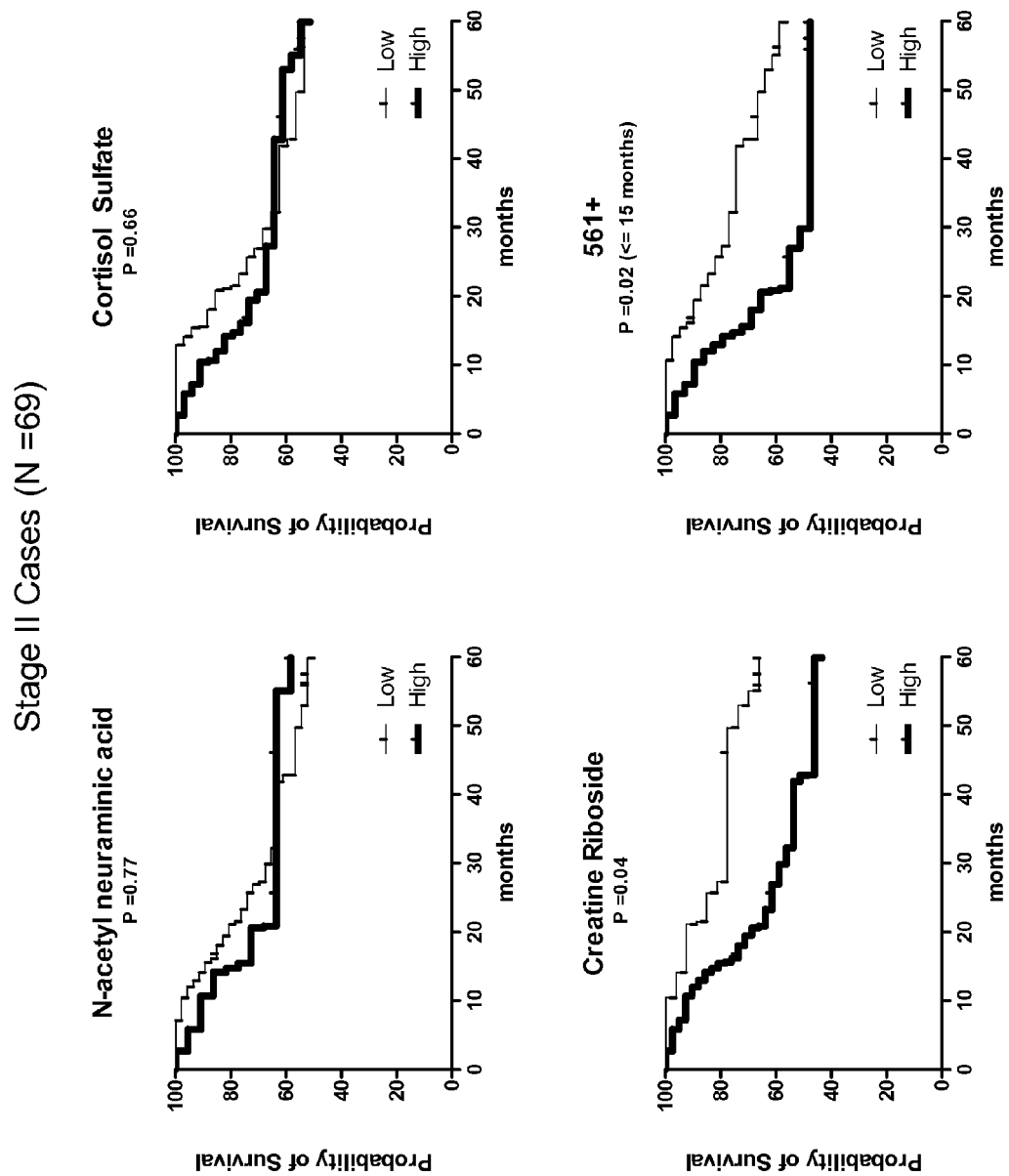
Figures 3, 12:
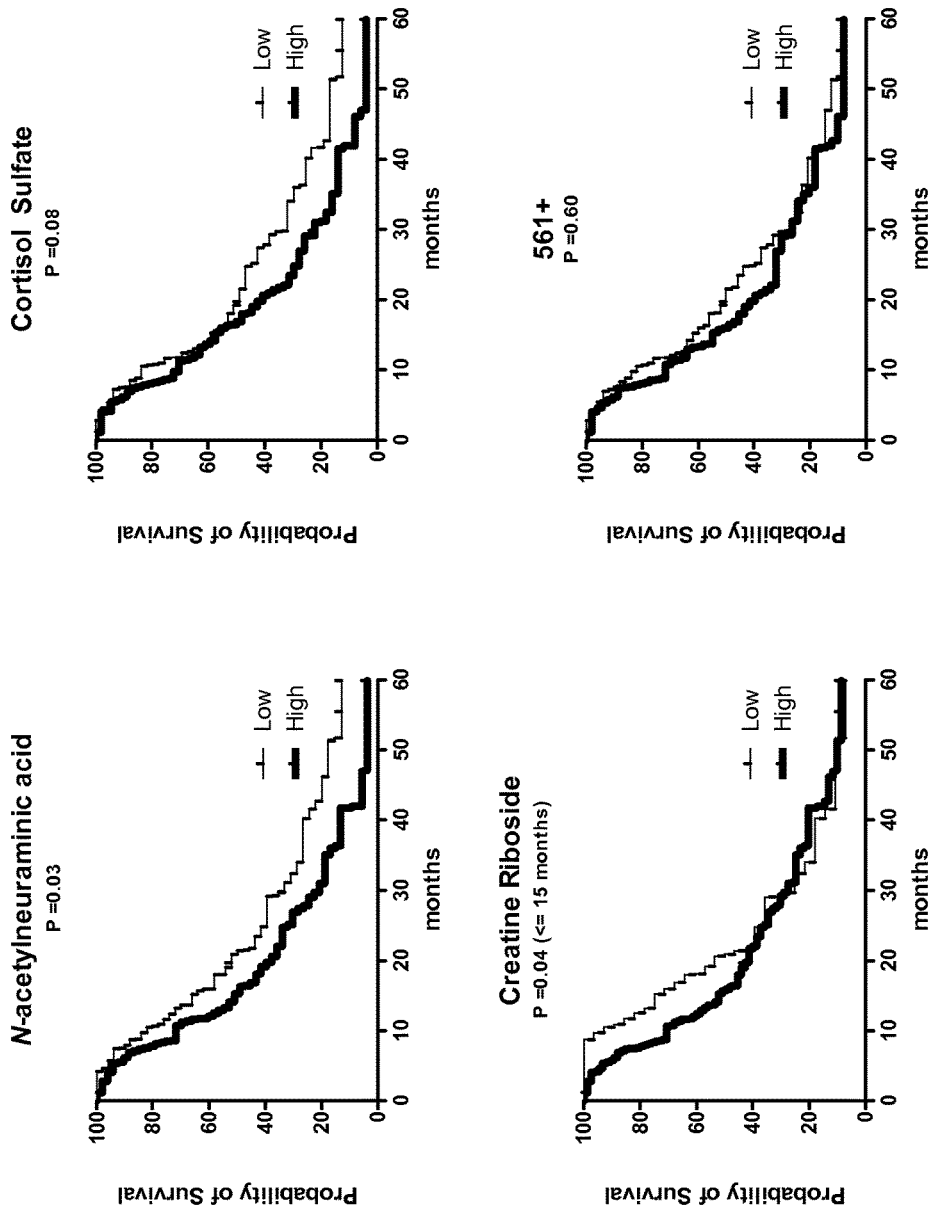

*Adjusted for gender, race, stage (unless stratified), histology, smoking status, pack years, interview year and urine collection time
†False discovery rate (FDR) based on Benjamini and Hochberg In early stage cases, creatine riboside (HR=1.83 (P=0.03)) and 561+(HR=9.33 (P=0.0006) in the first 15 months) are associated with survival, independent of aforementioned clinical variables (Table 4, FIG. 11B). Importantly, the combination of these metabolites and their associations with survival demonstrates an independent and additive effect (FIG. 11C). In advanced stages (III-IV), creatine riboside remains associated with survival, in addition to N-acetylneuraminic acid, and cortisol sulfate (FIG. 12). As shown below in Table 5, stratification by race highlights cortisol sulfate as being most strongly associated with survival in African Americans.

TABLE 5

Associations with survival in the training set, stratified by race.

| | All Cases | |  |  |
|---|---|---|---|---|
| | All Cases (N = 469) | | | |
| | Univariate | | Multivariate* | |
| Signal | HR (95% CI) | P | HR (95% CI) | P |
| N-acetyl neuraminic acid | | | | |
| <=15 months | 1.74 (1.22-2.48) | 0.002 | 1.57 (1.07-2.29) | 0.02 |
| >15 months | 1.14 (0.82-1.57) | 0.44 | 1.26 (0.90-1.78) | 0.19 |
| Cortisol sulfate | 1.53 (1.21-1.94) | 0.0004 | 1.49 (1.15-1.94) | 0.003 |

TABLE 5-continued

Associations with survival in the training set, stratified by race.

Creatine riboside

| | | | | |
|---|---|---|---|---|
| <=45 months | 2.05 (1.54-2.71) | <0.0001 | 1.76 (1.29-2.39) | 0.0003 |
| >45 months | 0.86 (0.38-1.95) | 0.72 | 0.79 (0.34-0.85) | 0.59 |
| 561+ | | | | |
| <=20 months | 2.32 (1.70-3.15) | <0.0001 | 1.97 (1.41-2.75) | <0.0001 |
| >20 months | 1.05 (0.70-1.55) | 0.83 | 0.88 (0.57-2.75) | 0.54 |

Caucasians

All Caucasians (N = 342)

| Signal | Univariate | | Multivariate* | |
|---|---|---|---|---|
| | HR (95% CI) | P | HR (95% CI) | P |

N-acetylneuraminic acid

| | | | | |
|---|---|---|---|---|
| <=15 months | 1.77 (1.23-2.56) | 0.002 | 1.22 (0.84-1.69) | 0.23 |
| >15 months | 0.73 (0.45-1.17) | 0.19 | 0.78 (0.28-2.21) | 0.64 |
| Cortisol sulfate | 1.22 (0.92-1.62) | 0.166 | 1.23 (0.90-1.67) | 0.20 |
| Creatine riboside | | | | |
| <=45 months | 1.97 (1.42-2.73) | <0.0001 | 1.66 (1.16-2.37) | 0.005 |
| >45 months | 0.95 (0.39-2.34) | 0.92 | 0.84 (0.34-2.09) | 0.71 |
| 561+ | | | | |
| <=20 months | 1.89 (1.31-2.72) | 0.0007 | 1.64 (1.10-2.45) | 0.02 |
| >20 months | 1.09 (0.67-1.76) | 0.72 | 0.96 (0.58-1.62) | 0.89 |

African Americans

All African Americans (N = 127)

| Signal | Univariate | | Multivariate* | |
|---|---|---|---|---|
| | HR (95% CI) | P | HR (95% CI) | P |
| N-acetylneuraminic acid | 1.66 (1.07-2.57) | 0.02 | 1.29 (0.73-2.28) | 0.38 |
| Cortisol sulfate | 2.80 (1.77-4.42) | <0.0001 | 3.89 (2.08-7.28) | <0.0001 |
| Creatine riboside | 1.89 (1.10-3.27) | 0.02 | 1.40 (0.72-2.72) | 0.33 |
| 561+ | | | | |
| <=20 months | 4.03 (2.07-7.84) | <0.0001 | 4.69 (2.12-10.40) | 0.0001 |
| >20 months | 0.87 (0.43-1.78) | 0.70 | 0.92 (0.40-2.12) | 0.85 |

Figures 1, 13:
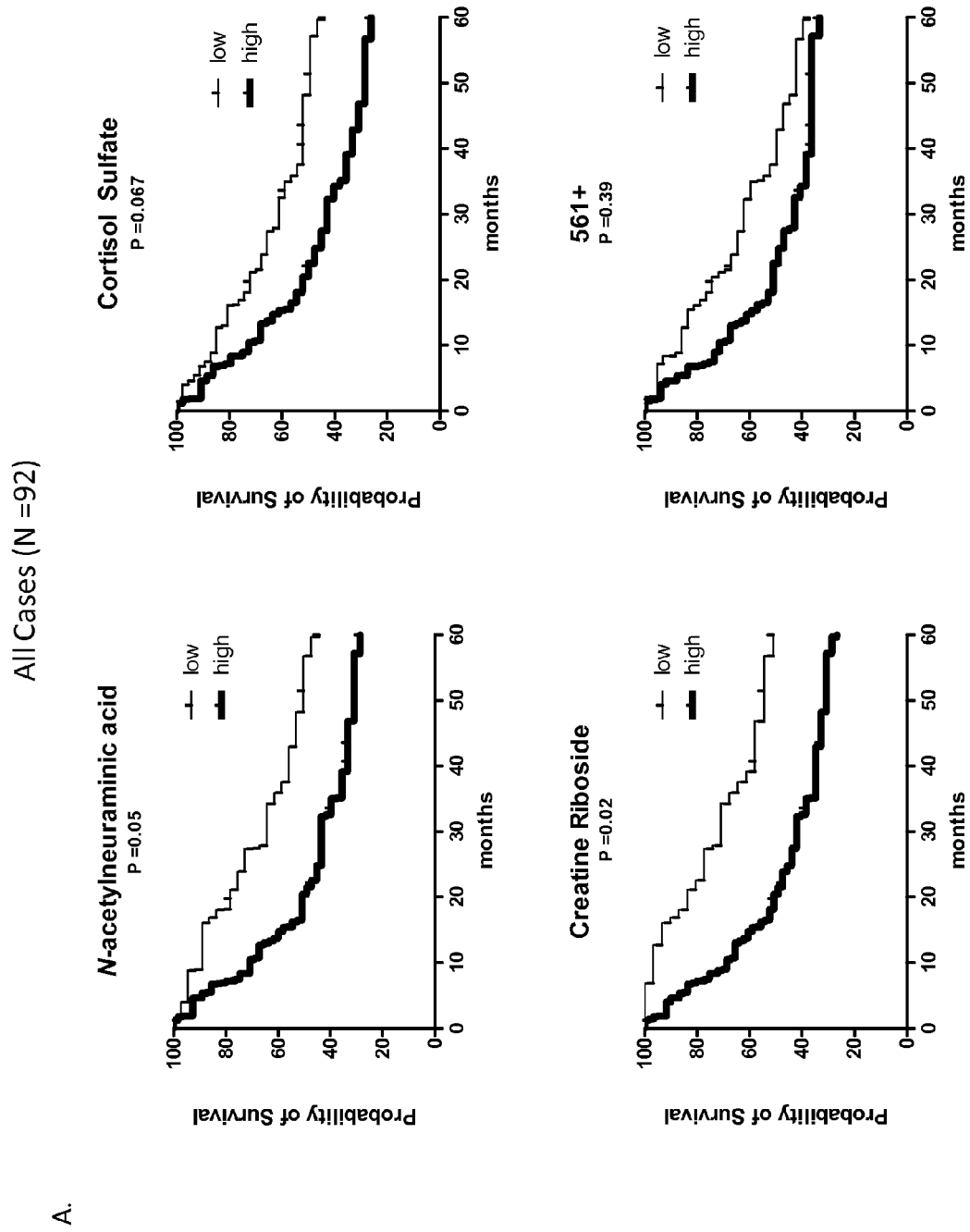
FIG. 13. Survival analysis of top four signals in the quantitation set containing representative 198 samples (92 cases, 106 controls), quantitated by UPLC-MS/MS. A) Kaplan Meier survival plots of individual metabolites and B) their combination. C) Cox proportional hazards regression results are depicted for all cases in the representative quantitation set (N=92).
Figures 2, 13:
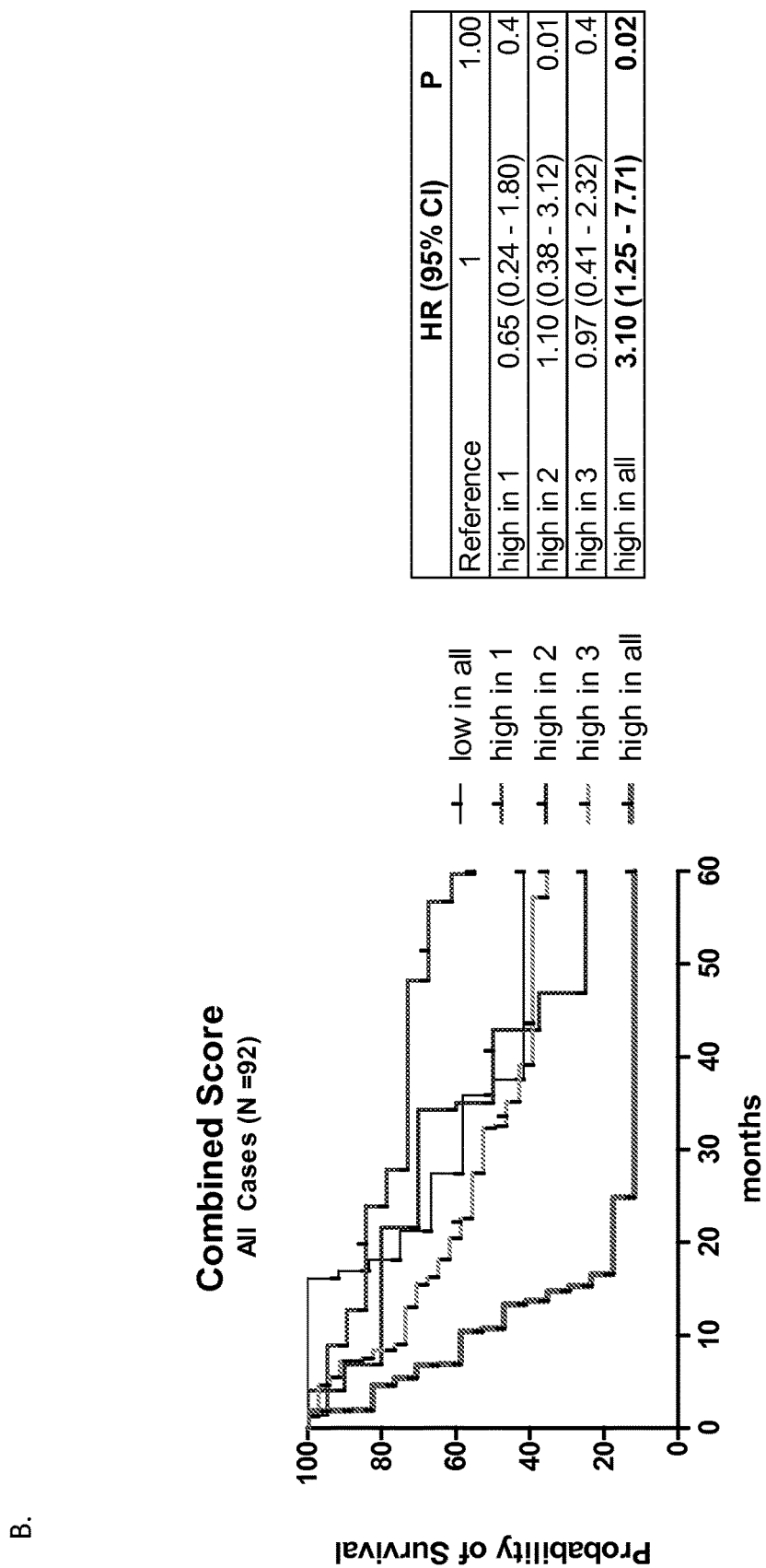

*Adjusted for gender, race (unless stratified), stage, histology, smoking status, pack years, interview year and urine collection time Associations were confirmed in the quantitation set comprising 198 samples (FIG. 13).

Example 6

This Example compares the levels of biomarkers of the present invention present in colon tumor tissue with the levels observed in non-cancerous tissue.

Global metabolomics analysis was conducted on 40 tumor and adjacent non-tumor tissue samples (Table 6).

TABLE 6

Colon cancer tissue set characteristics.

| | Tumor/Adjacent Normal Pairs (N = 40) |
|---|---|
| Age | (mean = 66.8) |
| >mean | 24 |
| <=mean | 16 |
| Histology | |
| adenocarcinoma | 31 |
| mucinous adenocarcinoma | 7 |
| squamous cell carcinoma | 1 |
| carcinoma | 1 |
| Gender | |
| Female | 21 |
| Male | 19 |
| Stage | |
| I-II | 22 |
| III-IV | 18 |

Figure 15:
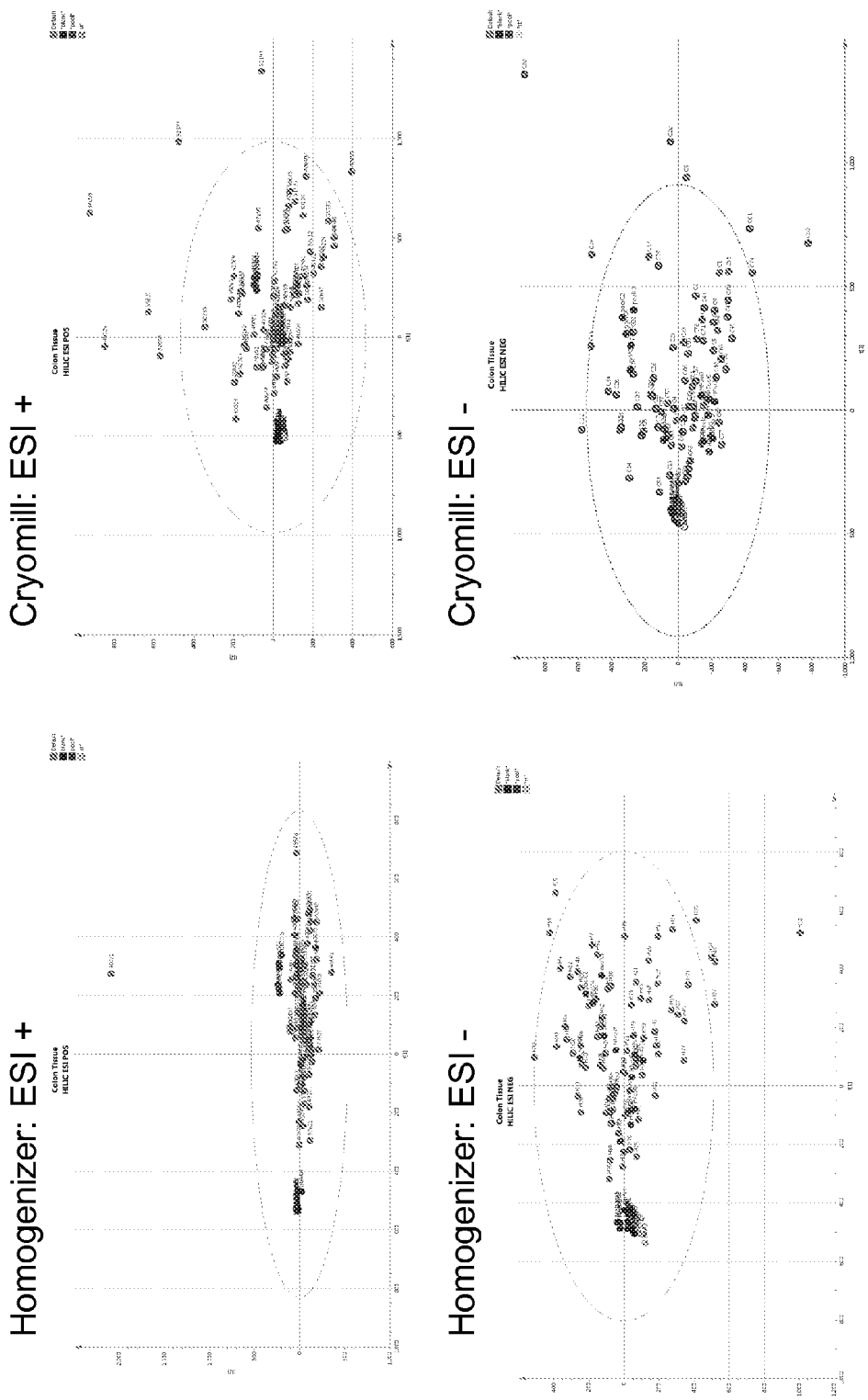
FIG. 15. Principal Component Analysis (PCA) of colon tumor and non-tumor tissue samples and quality controls (blank, metmix and cocktail containing internal standards).
Figure 16:
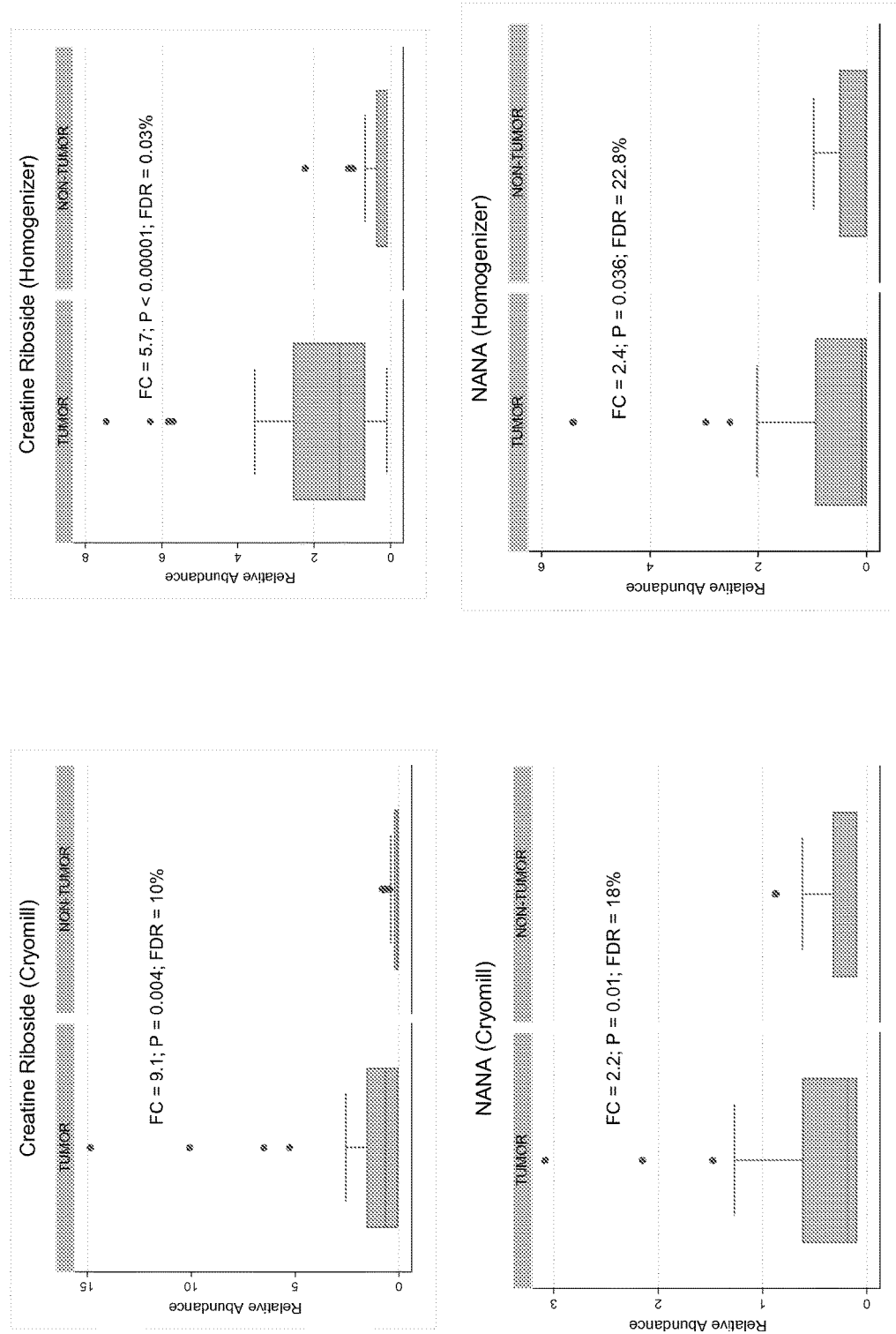
FIG. 16. Box plots of the relative levels of creatine riboside and NANA in 40 colon cancer matched tumor/non-tumor tissue pairs.

Average sample weight was 10 mg. Each tissue sample was processed twice, the first method using Cryogenic grinding, and the second method using tissue homogenization at room temperature. The first method consisted of cryogenic pulverization of tissue at ~−200° C. (Cryomill®, Retsch GmbH, Haan, Germany) using a 5 mm stainless steel ball. The second method consisted of tissue homogenization at room temperature using Precellys homogenizer (Bertin Technologies) and zirconium oxide beads (2.8 mm). Both methods were investigated as a form of a technical validation. In addition, the effect of variations in temperature during the extraction process on the stability of the metabolites of interest, creatine riboside and N-acetylneuraminic acid (NANA), was also investigated. After homogenization by both methods, metabolites were extracted as follows: a monophasic mixture of ice-cold chloroform:methanol:water (2:5:2, v:v:v) was used. Samples were centrifuged at 14,000×g for 15 minutes at 4° C., dried down using SpeedVac and reconstituted in 70% aqueous acetonitrile before they were injected onto the Xevo TQMS system. For the quality control purposes, blank, pooled and samples containing a cocktail of internal standards were included. A clustering of the quality control samples separately from the tissue samples indicates successful chromatography (FIG. 15). All samples were run on a quadrupole time-of-flight (QTOF) mass spectrometer (Premier, Waters), in positive (ESI+) and negative (ESI−) electrospray ionization modes, using hydrophilic interaction chromatography (HILIC) columns (Acquity UPLC BEH Amide 1.7 μm 50×2.1 mm) for a better separation of polar compounds. The levels of creatine riboside and NANA, which were previously found to be significantly upregulated in the urine and tumor tissue of lung cancer patients, were investigated and found to be upregulated in the colon tumor compared to adjacent non-tumor tissue (FIG. 16, reported P-values are based on the matched t-test). These findings indicate that these two metabolites are universally applicable as cancer markers.

Example 7

This Example examines the ability of the levels of biomarkers of the present invention in urine to diagnose and predict the prognosis of lung cancer.

Urine from 98 liver cancer cases frequency matched on age, gender and race to a 100 population controls, as well as 99 prostate cancer cases frequency matched on age and gender to 98 population controls was examined. Briefly, 250 μL, of urine was diluted 1:1 using 50% acetonitrile in water containing chloropropamide and aminopimelic acid as internal standards, vortexed briefly and spun for at 4° C. at 14,000×g 15 minutes. Samples were then chromatographed on a 50×2.1 mm Acquity BEH 1.7 μm C18 column using an ACQUITY UPLC™ system (WATERS®). MRM transitions were monitored using a XEVO® TQMS (WATERS®). In addition, samples were analyzed using hydrophilic interaction chromatography (HILIC) columns (ACQUITY UPLC™ BEH Amide 1.7 μm 50×2.1 mm) for the quantitation of creatine riboside and NANA. HILIC columns improve retention, separation, and detection of highly polar metabolites. All samples were normalized to creatinine levels to control for kidney function.

Figures 1, 18:
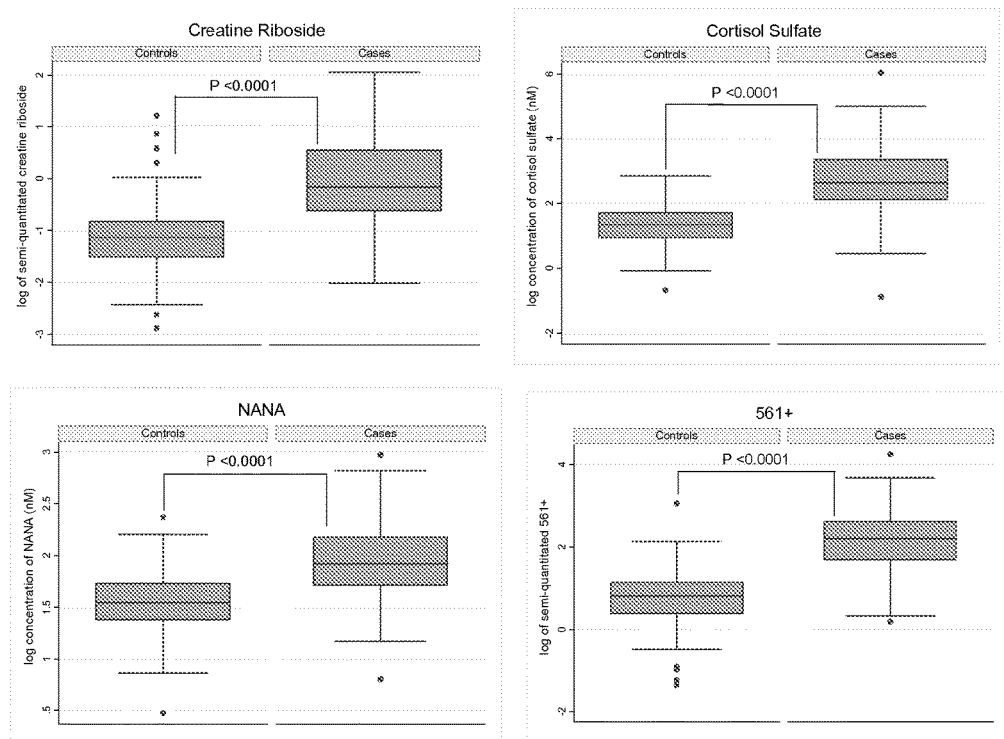
FIG. 18. Box plots depicting levels of metabolites in (A) liver cancer and (B) prostate cancer compared to their respective population controls. P-values depicted are results of Wilcoxon analysis.
Figures 2, 18:
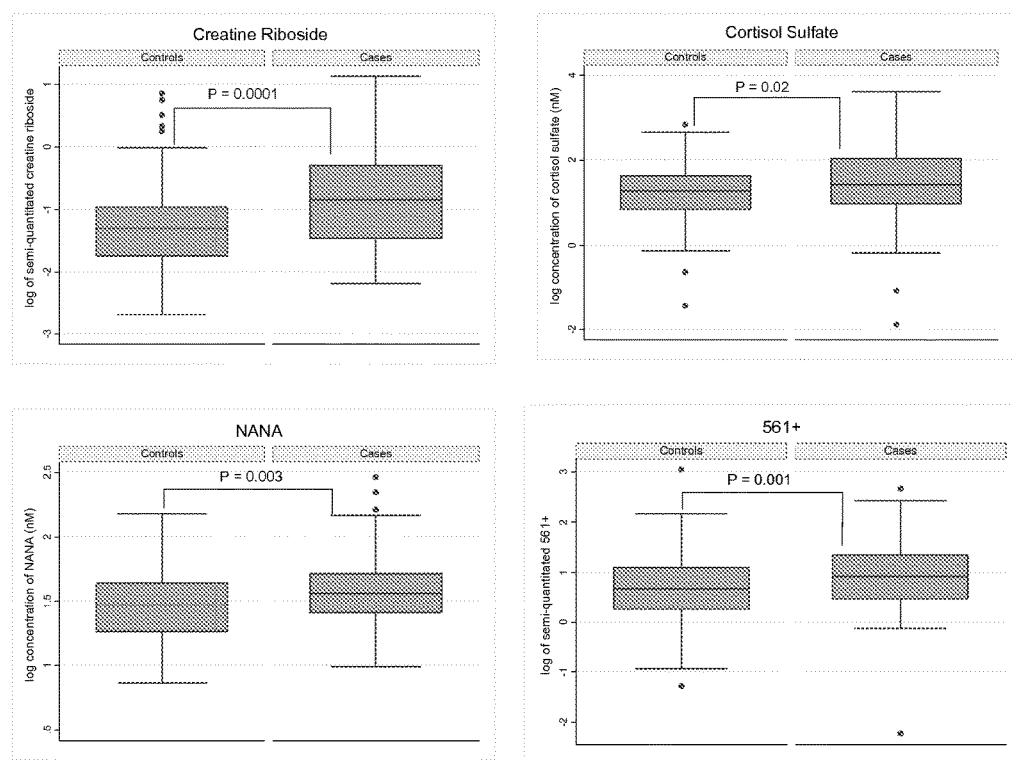

The results of these studies showed that high levels of all four metabolites, creatine riboside, cortisol sulfate, N-acetylneuraminic acid and 561+ were associated with lung cancer status (diagnosis) in the liver cases when compared to matched population controls (FIG. 17, top) after adjustment for potential confounding factors, race, gender, interview year, smoking status and pack years. In prostate cancer, high levels of cortisol sulfate are associated with lung cancer status (diagnosis) after adjustment for potential confounding factors, race, interview year, smoking status and pack years, while high levels of creatine riboside are borderline significant (P=0.08) (FIG. 17, bottom). Due to a limited number of cases and controls in this study, it is highly probable that we do not have the power to detect these associations in prostate cancer in the multivariate analysis after adjusting for potential confounders. However, odds ratios (ORs) show the same direction of the association as in lung cancer where these biomarkers were initially discovered. Furthermore, Wilcoxon analysis (FIG. 18) shows that all four metabolites are significantly (P<0.05) elevated in both liver and prostate cancer cases when compared to their matched population controls. The data presented herein indicates that the levels of creatine riboside, cortisol sulfate, N-acetylneuraminic acid and metabolite 561+ in the urine are useful in diagnosing cancer.

What is claimed:

1. A method for detecting creatine riboside in an individual, the method comprising:
   a) obtaining a sample from the individual; and,
   b) detecting whether creatine riboside is present in the sample using at least one method selected from the group consisting of:
   i) a method comprising column chromatography; and
   ii) a method comprising ionizing the sample so that if creatine riboside is present in the sample, creatine riboside ions are created, wherein the creatine riboside ions comprise an ion, or fragment ion, having a mass charge ratio of 264.1196+ or 90.0550+, and using mass spectrometry to detect the creatine riboside ions, if present.

2. The method of claim 1, wherein the sample is blood, serum, or plasma.

3. The method of claim 1, wherein the sample is urine.

4. The method of claim 1, comprising detecting at least one additional compound selected from the group consisting of metabolite 561+, cortisol sulfate, and N-acetylneuraminic acid.

5. The method of claim 1, wherein the assay comprises high pressure liquid chromatography (HPLC), and quadrupole time-of-flight (TOF) mass spectrometry.

6. The method of claim 5, wherein the HPLC is conducted using a C18 column.

7. A method of diagnosing and treating cancer in an individual, comprising:
   a) obtaining a sample from the individual; and,
   b) detecting whether creatine riboside is present in the sample using at least one method selected from the group consisting of:
   i) a method comprising column chromatography; and
   ii) a method comprising ionizing the sample so that if creatine riboside is present in the sample, creatine riboside ions are created, and using mass spectrometry to detect the creatine riboside ions, if present;
   c) diagnosing the individual as having cancer when creatine riboside is detected in the sample; and,
   d) administering an effective cancer therapy to the individual diagnosed as having cancer.

8. The method of claim 7, wherein the sample is a blood, serum, or plasma sample.

9. The method of claim 7, wherein the sample is a urine sample.

10. The method of claim 7, comprising determining the level of at least one additional compound selected from the group consisting of metabolite 561+, cortisol sulfate, and N-acetylneuraminic acid.

11. The method of claim 7, wherein the step of determining comprises using high pressure liquid chromatography (HPLC), and quadrupole time-of-flight (TOF) mass spectrometry.

12. The method of claim 11, wherein the HPLC is conducted using a C18 column.

13. The method of claim 7, wherein the creatine riboside ions comprise an ion, or fragment ion, having a mass to charge ratio of 264.1196+ or 90.0550+.

14. A method of determining the efficacy of a treatment for cancer in an individual, comprising:
 a. obtaining a first sample from the individual at a first time point;
 b. administering the cancer treatment to the individual;
 c. obtaining a second sample from the individual at a second time point;
 d. determining the level of creatine riboside in the first and second samples using at least one method selected from the group consisting of;
 i) a method comprising column chromatography; and,
 ii) a method comprising ionizing the sample, and using mass spectrometry to detect the creatine riboside ions, wherein the creatine riboside ions comprise an ion, or fragment ion, having a mass to charge ration of 264.1196+ or 90.0550+;
 e) comparing the level of creatine riboside in the first and second samples to determine the efficacy of the treatment.

15. The method of claim 14, wherein the sample is a blood sample, a serum sample, a plasma sample, or a urine sample.

16. The method of claim 14, comprising determining the level of at least one additional compound selected from the group consisting of metabolite 561+, cortisol sulfate, and N-acetylneuraminic acid.

17. The method of claim 7, wherein the therapy is surgical biopsy.

18. A method for identifying and treating an individual having cancer, the method comprising:
 a) detecting whether creatine riboside is present in a sample from an individual using at least one method selected from the group consisting of:
  i) a method comprising column chromatography; and
  ii) a method comprising ionizing the sample so that if creatine riboside is present in the sample, creatine riboside ions are created, and using mass spectrometry to detect the creatine riboside ions, if present;
 b) determining the level of creatine riboside in the individual;
 c) identifying the individual as having cancer when the level of creatine riboside is significantly higher than the level of creatine riboside observed in an individual without cancer; and,
 d) administering anti-cancer therapy to the individual identified as having cancer.

19. The method of claim 18, wherein the sample is selected form the group consisting of blood, serum, plasma, and urine.

20. The method of claim 18, comprising determining the level of at least one additional compound selected from the group consisting of metabolite 561+, cortisol sulfate, and N-acetylneuraminic acid.

* * * * *